(12) United States Patent
Sharma et al.

(10) Patent No.: US 12,005,157 B2
(45) Date of Patent: Jun. 11, 2024

(54) ISOLATION AND CO-TRANSPLANTATION OF BONE MARROW MESENCHYMAL STEM CELLS WITH CD34+ HEMATOPOIETIC STEM/PROGENITOR CELLS

(71) Applicants: Northwestern University, Evanston, IL (US); ANN & ROBERT H. LURIE CHILDREN'S HOSPITAL OF CHICAGO, Chicago, IL (US)

(72) Inventors: Arun Sharma, Elmwood Park, IL (US); Natalie J. Fuller, Chicago, IL (US); Matthew I. Bury, Delkalb, IL (US); Earl Y. Cheng, Elmhurst, IL (US)

(73) Assignees: Northwestern University, Evanston, IL (US); Ann & Robert H. Lurie Children's Hospital of Chicago, Chicago, IL (US)

( * ) Notice: Subject to any disclaimer, the term of this patent is extended or adjusted under 35 U.S.C. 154(b) by 736 days.

(21) Appl. No.: 14/625,168

(22) Filed: Feb. 18, 2015

(65) Prior Publication Data
US 2015/0231303 A1     Aug. 20, 2015

Related U.S. Application Data

(60) Provisional application No. 61/941,143, filed on Feb. 18, 2014.

(51) Int. Cl.
| | | |
|---|---|---|
| A61L 27/38 | (2006.01) | |
| A61L 27/54 | (2006.01) | |
| A61L 27/58 | (2006.01) | |

(52) U.S. Cl.
CPC .......... *A61L 27/3834* (2013.01); *A61L 27/54* (2013.01); *A61L 27/58* (2013.01); *A61L 2300/64* (2013.01); *A61L 2430/22* (2013.01); *A61L 2430/32* (2013.01)

(58) Field of Classification Search
None
See application file for complete search history.

(56) References Cited

U.S. PATENT DOCUMENTS

2010/0167316 A1 * 7/2010 Muschler ............. C12N 5/0663
435/7.21
2010/0316614 A1 * 12/2010 Sharma .................. A61K 35/28
424/93.7

OTHER PUBLICATIONS

Sharma et al. Co-transplantation with specific populations of spina bifida bone marrow stem/progenitor cells enhances urinary bladder regeneration, 2013.*
Kim (Stem Cell Therapy in Bladder Dysfunction, 2013) (Year: 2013).*
Elmi (Involvement of CD34+ Progenitor Cells in Regeneration of the Bladder Acellular Matrix Graft: Time-Dependent Neovasculogenesis and Regeneration of Different Bladder Wall Components, 2007) (Year: 2007).*
Atala et al., Tissue-engineered autologous bladders for patients needing cystoplasty, Lancet, 2006, 367:1241-1246.
Austin, Long-term risks of bladder augmentation in pediatric patients, Curr Opin Urol., 2008, 18:408-412.
Baum et al., Isolation of a candidate human hematopoietic stem-cell population. Proc Natl Acad Sci USA, 1992, 89:2804-2808.
Bebbington et al., Open fetal surgery for myelomeningocele, Prenat Diagn., 2011, 31:689-694.
Bexell et al., Bone marrow multipotent mesenchymal stroma cells act as pericyte-like migratory vehicles in experimental gliomas, Mol Ther, 2009, 17:183-190.
Bracci-Laudiero et al., CD34-positive cells in human umbilical cord blood express nerve growth factor and its specific receptor TrkA, J Neuroimmunol , 2003, 136:130-139.
Cathey et al., in Principles of Tissue Engineering (Third Edition), eds Lanza R, Langer R, Vacanti J. (Elsevier, USA), 2007, pp. 528-530.
Choi et al., Effects of intravesical electrical stimulation therapy on urodynamic patterns for children with spina bifida: A 10-year experience. J Pediatr Urol., 2012, S1477-5131(12)00257-4.
Clayton et al., Urologic management of spina bifida, Dev Disabil Res Rev, 2010, 16:88-95.
Flood et al., Long-term results and complications using augmentation cystoplasty in reconstructive urology, Neurourol Urodyn, 1995, 14:297-309.
Frontini et al., Fibroblast growth factor 9 delivery during angiogenesis produces durable, vasoresponsive microvessels wrapped by smooth muscle cells, Nat Biotechnol, 2011, 29:421-427.
Gao et al., A neuroinductive biomaterial based on dopamine, Proc Natl Acad Sci USA, 2006, 103:16681-16686.
Greene et al., Genetics of human neural tube defects, Hum Mol Genet, 2009, 18:R113-R129.
Guven et al., Spontaneous bladder perforations following augmentation cystoplasty in children, Nat Clin Pract Urol, 3:584-585.
Guys et al., Sacral neuromodulation for neurogenic bladder dysfunction in children, J Urol, 2004, 172:1673-1676.
Heinrich et al., Cytokine effects on gap junction communication and connexin expression in human bladder smooth muscle cells and suburothelial myofibroblasts, 2011, PLoS ONE, 6:e20792.
Hoogduijn et al, Functional nicotinic and muscarinic receptors on mesenchymal stem cells, 2011, Stem Cells Dev, 18:103-112.
Ishikane et al., Allogeneic injection of fetal membrane-derived mesenchymal stem cells induces therapeutic angiogenesis in a rat model of hind limb ischemia, Stem Cells, 2008, 26:2625-2633.
Losordo et al., Intramyocardial transplantation of autologous CD34+ stem cells for intractable angina: a phase I/IIa double-blind, randomized controlled trial, Circulation, 2007, 115:3165-3172.

(Continued)

*Primary Examiner* — Nghi V Nguyen
(74) *Attorney, Agent, or Firm* — Casimir Jones, S.C.; David W. Staple

(57) ABSTRACT

Provided herein are populations of bone marrow mesenchymal stem cells (MSCs) and CD34+ hematopoietic stem/progenitor cells (HSPCs), and methods of isolation and co-administration thereof. In particular, cell populations and methods of co-administration thereof are provided for enhancing tissue (e.g., bladder) regeneration.

10 Claims, 21 Drawing Sheets

(56) References Cited

OTHER PUBLICATIONS

Losordo et al., Intramyocardial, autologous CD34+ cell therapy for refractory angina, Circ Res, 2011, 109:428-436.
Mezey et al., Turning blood into brain: cells bearing neuronal antigens generated in vivo from bone marrow. Science, 2000, 290:1779-1782.
Murphy et al., Nanoparticle-mediated drug delivery to tumor vasculature suppresses metastasis, Proc Natl Acad Sci USA, 2008, 105:9343-9348.
Nagatomi et al., Quantification of bladder smooth muscle orientation in normal and spinal cord injured rats, Ann Biomed Eng., 2005, 33:1078-1089.
Pittenger et al., Multilineage potential of adult human mesenchymal stem cells. Science, 1999, 284:143-147.
Sahoo et al., Exosomes from human CD34(+) stem cells mediate their proangiogenic paracrine activity, Circ Res, 2011, 109:724-728.
Scheubel et al., Paracrine effects of CD34 progenitor cells on angiogenic endothelial sprouting, Int J Cardiol., 2010, 139:134-141.
Sharma et al., Defined populations of bone marrow derived mesenchymal stem and endothelial progenitor cells for urinary bladder regeneration, J Urol, 2009, 182:1898-1905.
Sharma et al., Urinary bladder smooth muscle regeneration utilizing bone marrow derived mesenchymal stem cell seeded elastomeric poly(1,8-octanediol-co-citrate) based thin films, Biomaterials, 2010, 31:6207-6217.
Shin et al., Hedgehog/Wnt feedback supports regenerative proliferation of epithelial stem cells in bladder, Nature, 2011, 472:110-114.
Spiegel et al., Catecholaminergic neurotransmitters regulate migration and repopulation of immature human CD34+ cells through Wnt signaling, Nat Immunol, 2007, 8:1123-1131.
Stegemann et al., Review: advances in vascular tissue engineering using protein-based biomaterials, Tissue Eng, 2007, 13:2601-2613.
Steidl et al., Primary human CD34+ hematopoietic stem and progenitor cells express functionally active receptors of neuromediators. Blood, 2004, 104:81-88.
Takeda et al., Normal bladder wall morphology in Gd-DTPA-enhanced clinical MR imaging using an endorectal surface coil and histological assessment of submucosal linear enhancement using [14C]Gd-DOTA autoradiography in an animal model, Eur J Radiol, 1998, 26:290-296.
Tei et al., Administrations of peripheral blood CD34-positive cells contribute to medial collateral ligament healing via vasculogenesis, Stem Cells, 2008, 26:819-830.
Van Den Berg et al., Role of members of the Wnt gene family in human hematopoiesis, Blood, 1998, 92:3189-3202.
Xiao et al., An artificial somatic-central nervous system-autonomic reflex pathway for controllable micturition after spinal cord injury: preliminary results in 15 patients, J Urol, 2003, 170:1237-1241.

\* cited by examiner

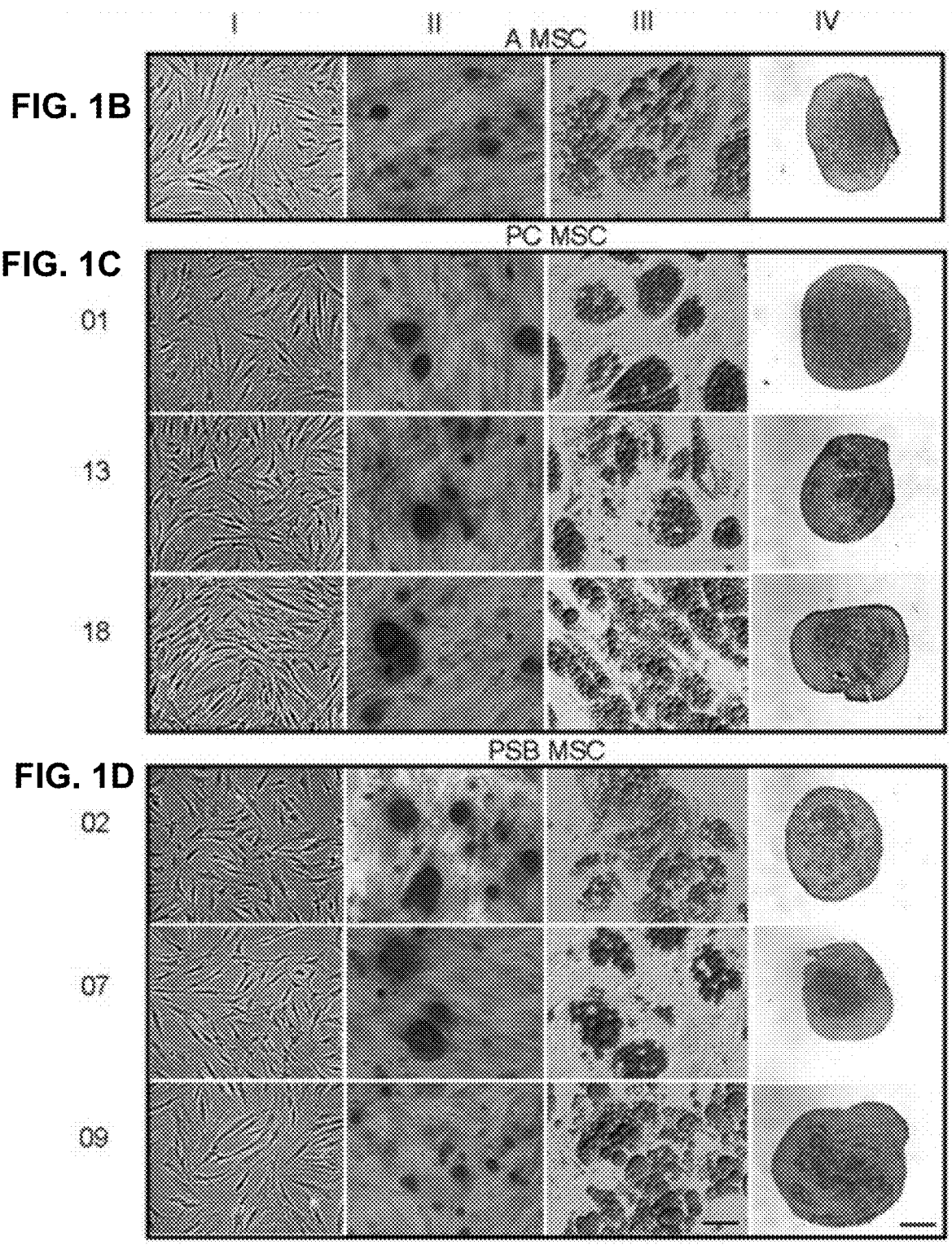

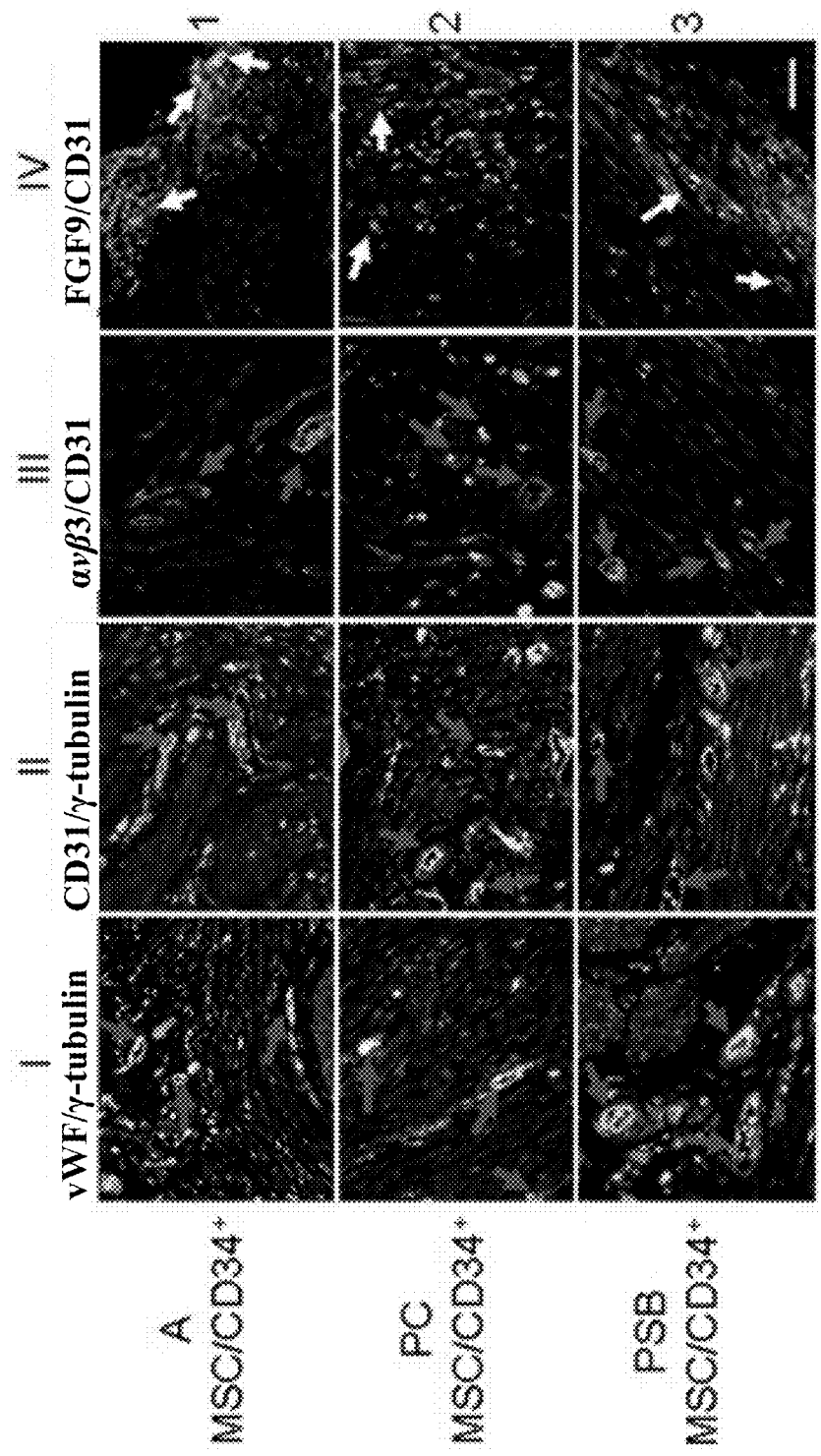

FIG. 3C

Percent vasculature for native and regenerated tissue

| | Unseeded | Four weeks | | | | | | | | | Ten weeks | | |
| --- | --- | --- | --- | --- | --- | --- | --- | --- | --- | --- | --- | --- | --- |
| | | MSC | A CD34+ | MSC/ CD34+ | MSC | PC CD34+ | MSC/ CD34+ | MSC | PBB CD34+ | MSC/ CD34+ | A MSC | PC MSC | PBB MSC |
| Native tissue (%) | 2.31 ±0.12 | 2.73 ±0.54 | 2.89 ±0.23 | 1.70 ±0.38 | 2.89 ±0.15 | 2.88 ±0.27 | 2.43 ±0.12 | 2.89 ±0.11 | 2.27 ±0.06 | 2.15 ±0.47 | 3.01 ±0.41 | 2.98 ±0.28 | 2.92 ±0.30 |
| Regenerated tissue (%) | 1.07 ±0.10 | 1.46 ±0.16*** | 3.27 ±0.31*** | 8.60 ±0.57 | 1.62 ±0.21*** | 4.07 ±0.64*** | 7.20 ±0.22 | 1.67 ±0.21*** | 4.20 ±0.28*** | 8.81 ±1.40 | 1.77 ±0.23 | 2.01 ±0.18 | 1.70 ±0.10 |

Quantification of in vivo proliferation in grafted cells.

| Ki-67 index (%) for grafted cell populations (hu-reactive γ-tubulin+ cells) | Graft duration in vivo / Grafted cell type(s) | | | |
|---|---|---|---|---|
| | Four weeks | | | Ten weeks |
| | CD34+ | MSC/CD34+ | MSC | MSC |
| A | 7.7±3.9 | 60.4±1.0 | 65.5±0.8 | 24.0±1.5* |
| PC | 11.1±1.2 | 62.6±1.3 | 64.8±1.0 | 23.3±0.9** |
| PSB | 9.2±1.7 | 64.4±0.9 | 66.4±0.8 | 24.6±1.1*** |

ISOLATION AND CO-TRANSPLANTATION OF BONE MARROW MESENCHYMAL STEM CELLS WITH CD34+ HEMATOPOIETIC STEM/PROGENITOR CELLS

CROSS REFERENCE TO RELATED APPLICATIONS

The present application claims the benefit of U.S. Provisional Patent Application Ser. No. 61/941,143, filed Feb. 18, 2014, which is incorporated by reference in its entirety.

FIELD

Provided herein are populations of bone marrow mesenchymal stem cells (MSCs) and CD34+ hematopoietic stem/progenitor cells (HSPCs), and methods of isolation and co-administration thereof. In particular, cell populations and methods of co-administration thereof are provided for enhancing tissue (e.g., bladder) regeneration.

BACKGROUND

The most common neural tube defect compatible with life presents itself as spina bifida (SB) and consists of three disparate subtypes of which myelomeningocele is the most common and the most debilitating (refs. 1, 2; herein incorporated by reference in their entireties). SB patients affected by myelomeningocele non-exclusively suffer from bowel and urinary bladder abnormalities as a consequence of developmental error (ref 3; herein incorporated by reference in its entirety). The resulting neurogenic bladder predisposes a poor clinical outcome in which bladder function is below acceptable levels leading to renal insufficiencies and ultimate renal failure (ref 4; herein incorporated by reference in its entirety). In order to alleviate pressure from the upper urinary tract, patients undergo surgical intervention in the form of bladder augmentation enterocystoplasty in which a segment of bowel is utilized as a "patch" to enhance physiological bladder parameters to protect kidney function (FIG. 1A, top). However, this procedure is associated with many side effects including electrolyte imbalance, perforation, infection, stone formation, incontinence, and the potential of malignant transformation (refs. 5-7; herein incorporated by reference in their entireties). Attempts to recreate functional bladder tissue ex vivo have been met with numerous obstacles that encompass materials design issues and cellular incompatibilities.

SUMMARY

Provided herein are populations of bone marrow mesenchymal stem cells (MSCs) and CD34+ hematopoietic stem/progenitor cells (HSPCs), and methods of isolation and co-administration thereof. In particular, cell populations and methods of co-administration thereof are provided for enhancing tissue (e.g., bladder) regeneration.

In some embodiments, the present invention provides isolated cell populations comprising mesenchymal stem cells (MSCs), wherein greater than 50% of the cells in said population are $CD29^+$, $CD44^+$, $CD73^+$, $CD90^+$, $CD105^+$, $CD166^+$, $CD14^-$, $CD34^-$, $CD45^-$, $CD117^-$, and $CD133^-$ MSCs (e.g., >60% ... >70% ... >80% ... >90% ... >95% ... >98% ... >99% ... >99.5% ... >99.9%, or more).

In some embodiments, the present invention provides systems comprising: (a) a scaffold for supporting and transplant of cells, (b) a cell population wherein greater than 50% of the cells in said population are $CD29^+$, $CD44^+$, $CD73^+$, $CD90^+$, $CD105^+$, $CD166^+$, $CD14^-$, $CD34^-$, $CD45^-$, $CD117^-$, and $CD133^-$ MSCs (e.g., >60% ... >70% ... >80% ... >90% ... >95% ... >98% ... >99% ... >99.5% ... >99.9%, or more); and a cell population of $CD34^+$ hematopoietic stem/progenitor cells (HSPCs). In some embodiments, greater than 50% of the cells in the cell population of $CD34^+$ HSPCs are $CD34^+$ HSPCs (e.g., >60% ... >70% ... >80% ... >90% ... >95% ... >98% ... >99% ... >99.5% ... >99.9%, or more). In some embodiments, the scaffold comprises a poly(citrate diol).

In some embodiments, the present invention provides methods of tissue regeneration comprising administering to a subject in need of tissue repair (i) a cell population comprising greater than 50% (e.g., >50%, >60%, >70%, >80%, >90%, >95%, >98%, >99%, or more) MSCs (e.g., $CD29^+$, $CD44^+$, $CD73^+$, $CD90^+$, $CD105^+$, $CD166^+$, $CD14^-$, $CD34^-$, $CD45^-$, $CD117^-$, and/or $CD133^-$ MSCs), and (ii) a cell population comprising greater than 50% (e.g., >50%, >60%, >70%, >80%, >90%, >95%, >98%, >99%, or more) $CD34^+$ HSPCs. In some embodiments, the cell populations of (i) and (ii) are loaded onto a support scaffold. In some embodiments, the scaffold comprises a poly(diol citrate). In some embodiments, the scaffold comprises poly(octanediol citrate). In some embodiments, the tissue is bladder tissue.

BRIEF DESCRIPTION OF THE DRAWINGS

FIG. 1A-D shows MSC characterization. (A) Schematic representation of standard bladder augmentation procedure (top panel) along with the alternative urinary bladder tissue patch procedure (bottom panel). (B-D) Donor MSCs demonstrated expected osteogenic (column II), adipogenic (column III), and chondrogenic (column IV) differentiation via lineage specific staining along with undifferentiated controls (column I). 400× magnification; scale bar-50 µm (images B-D). 100× magnification; scale bar-200 µm (chondrocytes).

FIG. 3A-C shows vascular regeneration in $MSC/CD34^+$ grafts. (A) $\gamma$-tubulin$_+$/$vWF^+$ (column I) and $\gamma$-tubulin$^+$/$CD31^+$ (column II) cells were detected in regenerated tissue. Presence of $\alpha v \beta 3^+/CD31^+$ and $FGF9^+/CD31^+$ (columns III, IV respectively) cells provide evidence of angiogenesis. Blue-DAPI. Dark arrows: co-localization of markers, whit arrows: new vessel growth. Scale bar=50 µm. (B) Regenerated tissue in $MSC/CD34^+$ grafts demonstrated higher numbers of vessels and percent vasculature than MSC and CD34+ graft tissue 4 weeks post-augmentation. Data shown as mean±SE; *p<0.01p<0.001*p≤0.0001 for MSC/CD34+ vs MSC and CD34+ groups (4 weeks).

DEFINITIONS

Figure 1A:
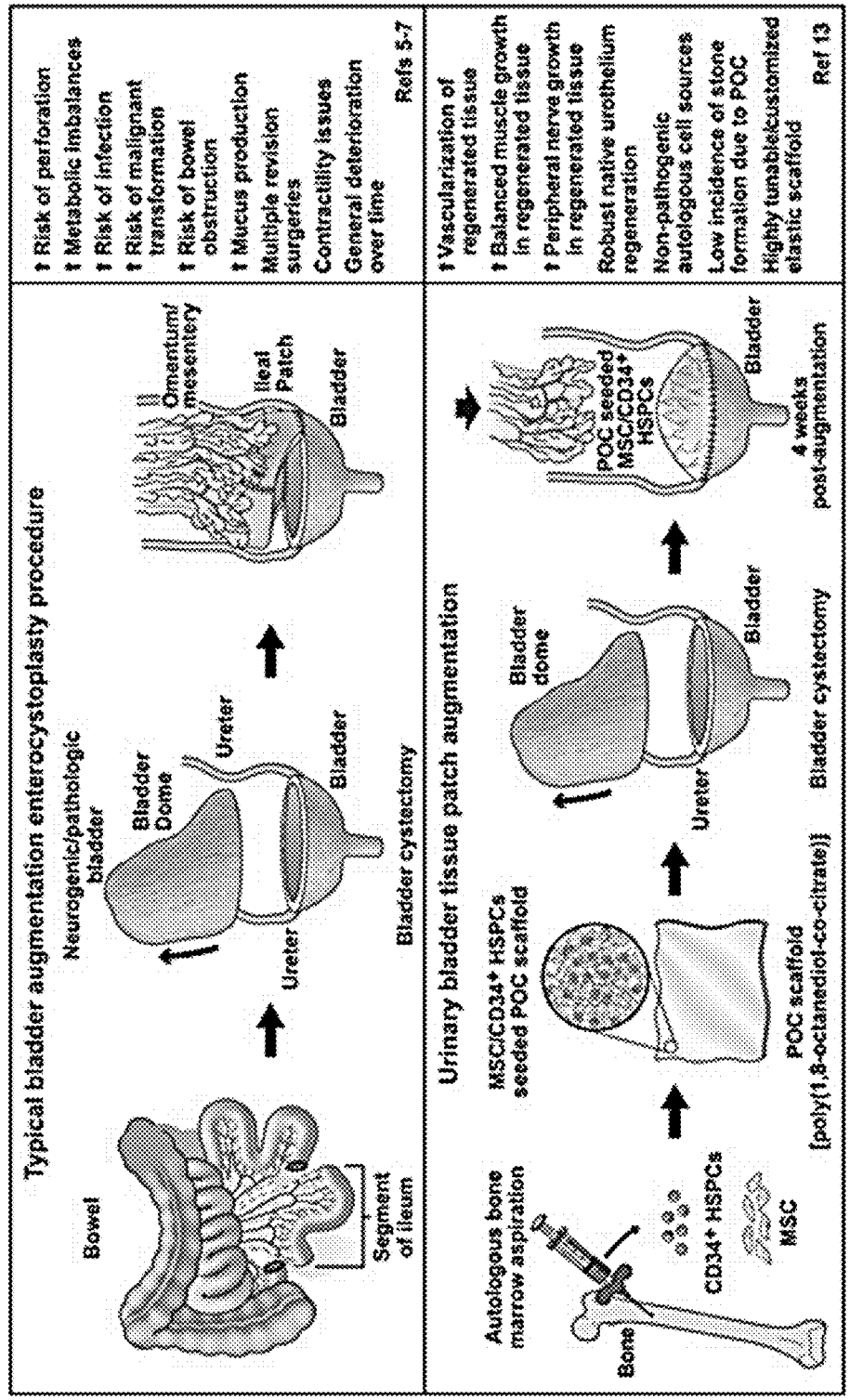

To facilitate an understanding of the present invention, a number of terms and phrases are defined below:

The term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual.

As used herein, the term "stem cell" or "undifferentiated cell" refers to self-renewing multipotent cells that are capable of giving rise to more stem cells, as well as to various types of terminally differentiated cells.

As used herein, the term "host" refers to any warm blooded mammal, including, but not limited to, humans, non-human primates, rodents, and the like, which is to be the recipient of a particular treatment. Typically, the terms "host" and "patient" are used interchangeably herein in reference to a human subject.

As used herein, the terms "defective tissues" and "defective cells" refer to tissues and cells that are marked by subnormal structure, function, or behavior. Defects responsible for the defective tissues and cells include known or detectable defects, as well as, unknown or undetectable defects.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, ayes, etc.

The term "biologically active," as used herein, refers to a protein or other biologically active molecules (e.g., catalytic RNA) having structural, regulatory, or biochemical functions of a naturally occurring molecule.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "isolated" when used in relation to a cell, as in "an isolated cell" or "isolated cells" refers to cells that are separated and enriched in a sample so as to remove the isolated cell(s) from other cells with which it is ordinarily associated in its natural environment. For example, isolated stem cells are stem cells that are removed from their natural environment and enriched in a sample, such that the sample housing the stem cells contains a higher percentage of stem cells than a corresponding sample found in a tissue in its natural environment.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue (e.g., tissues of the gut or central nervous system), liquid foods (e.g., milk), and solid foods (e.g., vegetables).

As used herein, "culturing" refers to propagating or nurturing a cell, collection of cells, tissue, or organ, by incubating for a period of time in an environment and under conditions which support cell viability or propagation. Culturing can include one or more of the steps of expanding and proliferating a cell, collection of cells, tissue, or organ according to the invention.

As used herein, the term "uncultured cells" refers to cells in in vivo context or that have been isolated from the in vivo context, but not submitted to culture conditions.

As used herein, a "recipient" refers to a mammal that receives an organ, tissue or cells taken from a donor. As used herein, a "donor" is a mammal from which organs, tissues or cells are taken for transplant into a recipient. In the case of autologous stem cells, the donor and recipient are the same subject.

DETAILED DESCRIPTION

Provided herein are populations of bone marrow mesenchymal stem cells (MSCs) and CD34+ hematopoietic stem/progenitor cells (HSPCs), and methods of isolation and co-administration thereof. In particular, cell populations and methods of co-administration thereof are provided for enhancing tissue (e.g., bladder) regeneration.

Experiments were conducted during development of embodiments of the present invention to demonstrate the role of two specific populations of bone marrow (BM) stem/progenitor cells, for example, used in combination with a synthetic elastomeric scaffold, provide methods for tissue (e.g., bladder) regeneration. In vitro differentiation, gene expression and proliferation was similar amongst donor mesenchymal stem cells (MSCs), while poly(1,8-octanediol-co-citrate) [POC] scaffolds seeded with SB BM MSCs perform analogously to control counterparts with regard to bladder smooth muscle wall formation in vivo. SB CD34$^+$ hematopoietic stem/progenitor cells (HSPCs) co-transplanted with donor matched MSCs cause a dramatic increase in tissue vascularization as well as an induction of peripheral nerve growth in grafted areas as compared to non-HSPC seeded samples. MSC/CD34$^+$ grafts provided the impetus for rapid urothelium regeneration. Data indicate that autologous BM stem/progenitor cells utilized as alternate, non-pathogenic cell sources for SB patient-specific bladder tissue regeneration, which provides an alternative to the currently used enterocystoplasty procedures.

The placement of MSCs in proximity with the CD34$^+$ HSPCs in vivo had a tremendous positive impact on vascular and peripheral nerve regeneration. In some embodiments, as a result of the impact on vascular and peripheral nerve regeneration this cell combination finds use in additional settings to those explicitly described herein in which peripheral nerve and vascularization are desired.

Primitive multipotent CD34+ HSPCs (or CD34+) have demonstrated the ability to differentiate into various cellular constituents of blood under appropriate environmental stimuli (ref. 8; herein incorporated by reference in its entirety). CD34+ HSPCs also have the unique ability to either induce angiogenesis or vasculogenesis by mechanisms that have not been fully delineated as demonstrated by neovascularization and physiological enhancement of ischemic myocardium (ref. 9; herein incorporated by reference in its entirety). Multipotent mesenchymal stem cells (MSCs) have been highly studied over the last several decades and maintain a level of self-renewal with attributes that allow for the terminal differentiation into what are now widely characterized cell types (ref 10; herein incorporated by reference in its entirety). Functional studies in multiple settings further demonstrate that MSCs also possess the unique ability to provide compensatory factors to damaged tissue by aiding in tissue repair exhibited by increased localized angiogenesis (ref 11; herein incorporated by reference in its entirety). Experiments conducted during development of embodiments of the present invention establish that SB BM MSCs are not affected by pathologies associated with SB and can perform analogously to control MSC counterparts within a nude rat bladder augmentation model. Experiments conducted during development of embodiments of the present invention further demonstrate that donor-matched SB MSCs with CD34+ HSPCs lead to superior blood vessel formation, peripheral nerve and robust urothelium regeneration in vivo. Hence, SB BM stem/progenitor cells provide distinct advantages over native bladder cells from SB patients as MSC/CD34+POC composites may provide an alternative solution to current bladder augmentation enterocystoplasty strategies.

Experiments conducted during development of embodiments of the present invention demonstrated several findings that describe the therapeutic potential of autologous sources of BM cells that could aid in tissue (e.g., bladder) regeneration. In some embodiments, procedures described herein provide an alternative to bladder augmentation cystoplasty for patients who maintain a normal bone marrow microenvironment such as those suffering from bladder trauma or localized bladder cancer. SB derived MSCs function analogously to both age-matched counterparts as well as adult MSCs under in vitro and in vivo conditions. Specifically, SB derived MSCs function as a surrogate cell source for the musculature of the bladder wall. The addition of donor matched CD34+ HSPCs to MSC seeded constructs contributes to two facets of bladder tissue engineering that have been sorely lacking to date. The striking level of putative blood vessel formation and peripheral nerve growth in grafted areas demonstrated by MSC/CD34+ seeded grafts, including those of SB origin, commenced at a very early timepoint in the regenerative process.

Figure 11A:
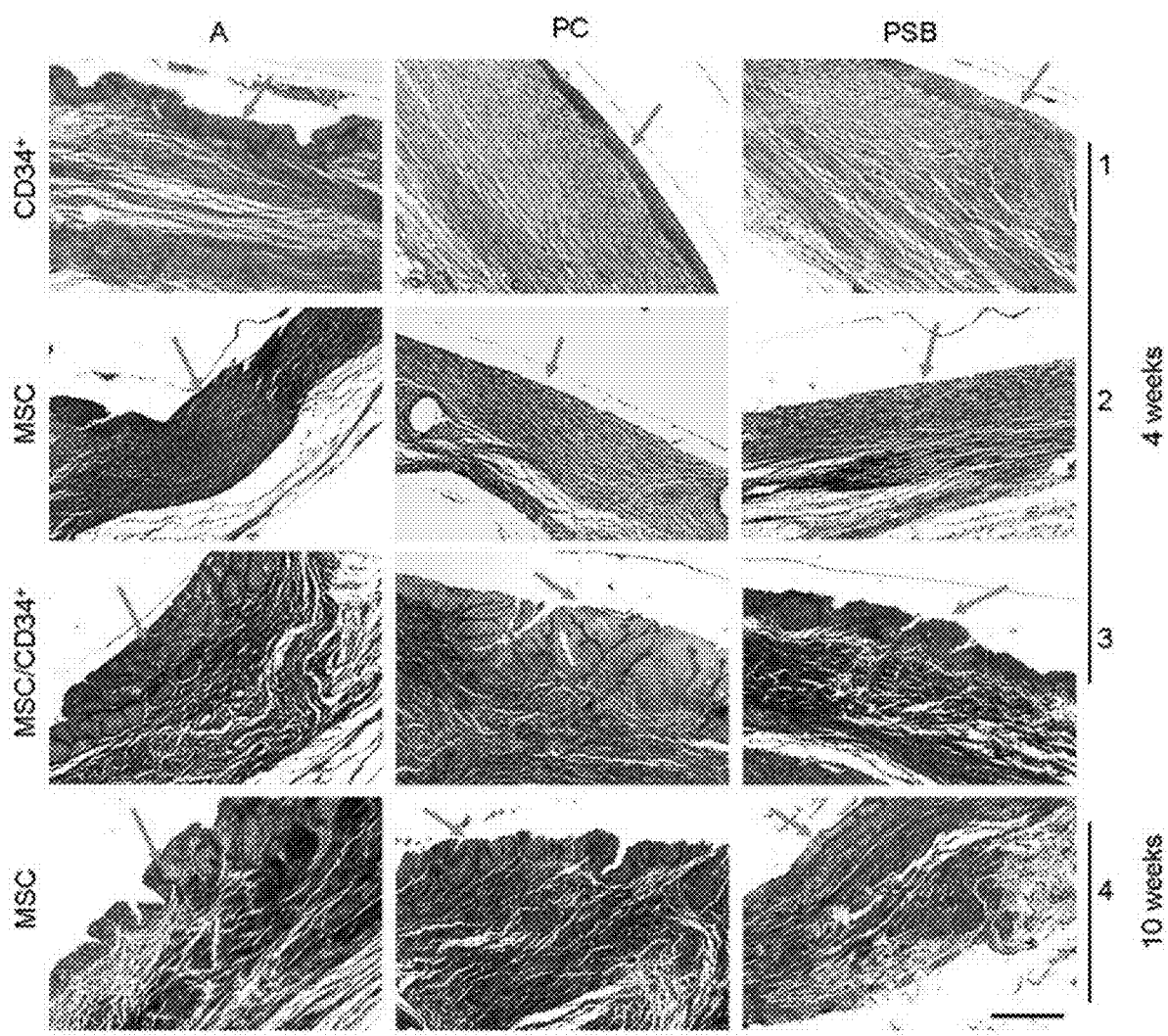
FIG. 11A shows urothelium regeneration of explanted POC/cell composites. One physiological aspect of the urothelium is to provide an effective, impermeable barrier against urine. This is accomplished in part by the expression and regulation of intercellular urothelial proteins in the form of tight junctions. Hence, the lack of a properly organized urothelium leads to an ineffective barrier against urine which facilitates leakage into the abdominopelvic cavity causing peritonitis and subsequent infection. Images in row 1 depict explanted CD34$^+$ HSPC scaffolds 4 weeks post-augmentation which display a thin layer of native urothelium in an area of regeneration. The converse is demonstrated in MSC seeded scaffolds (row 2) at the same timepoint where a suboptimal and tenuous urothelial layer is present. Note the lack of structural organization corroborated quantitatively by poor muscle/collagen ratios in both cell types evident in all donor groups. The combination of MSC/CD34$^+$ HSPCs at 4 weeks post-augmentation provides the most robust urothelial growth output of native urothelium in regenerated areas (row 3). The degree of urothelium thickness is similar to that of normal bladder tissue (FIG. 11a) as well as MSC seeded scaffolds 10 weeks post-augmentation across all donor groups (row 4). Bladder architecture appears normal including defined muscle fascicles with an approximate 1:1 ratio of muscle/collagen. Data indicates that the addition of CD34$^+$ HSPCs to MSC containing grafts contributes to the heightened regenerative capacity of the urothelium. Samples stained with Masson's Trichrome. Arrows indicate urothelium. Images are representative of multiple animal bladder samples. Scale bar-250 µm
Figure 11B:
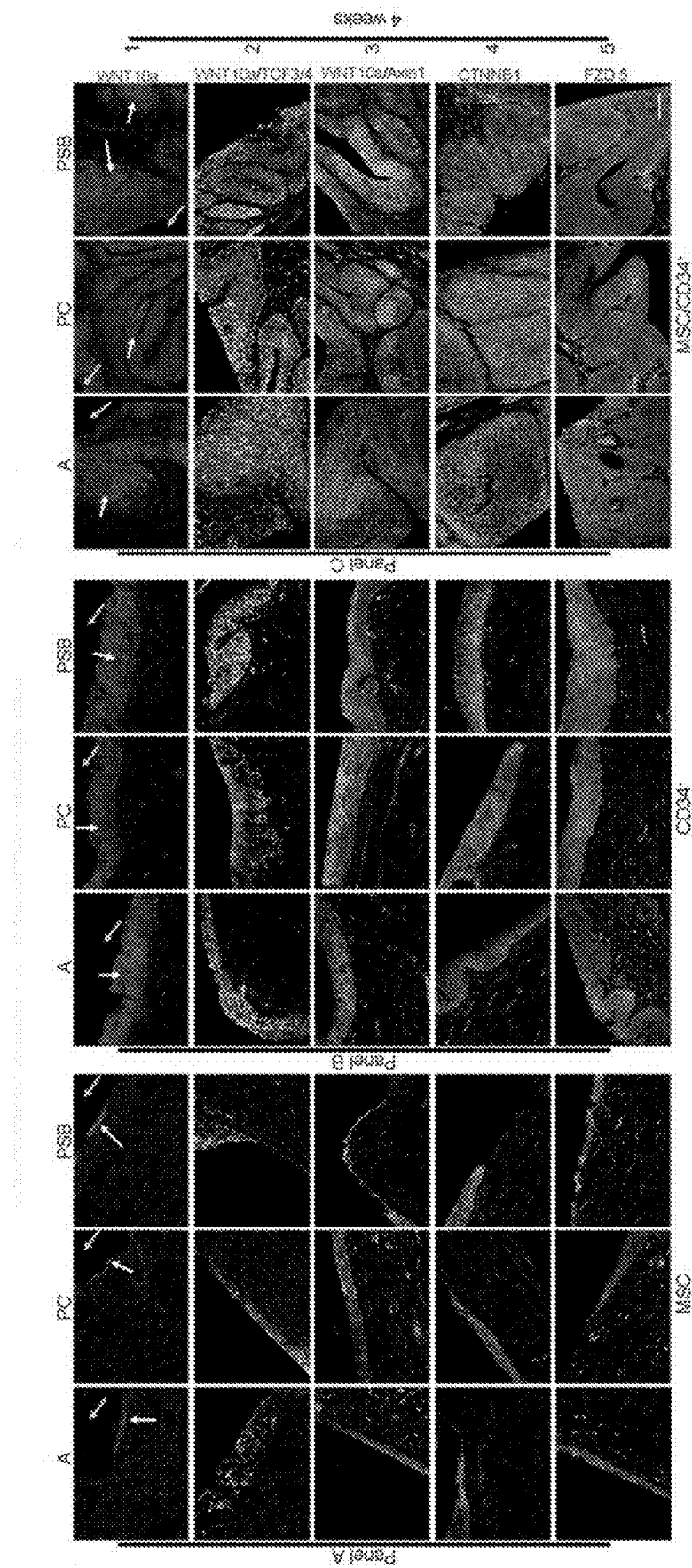
FIG. 11B shows Wnt proteins are upregulated in regenerating urothelium. Members of the Wnt family of proteins have been associated with pleiotropic effects in a variety of biological systems within differing organisms. These highly conserved proteins have also been implicated in stem cell self-renewal affiliated tissue regeneration. Within the context of this experiment, it was demonstrated that specific members of the Wnt family contribute to rapid and robust native urothelial regeneration in conjunction with seeded bone marrow cells. MSC seeded POC scaffolds (Panel A) demonstrate a mild regenerative response of native urothelium as demonstrated by Wnt10a expression (demarcated by white arrows, row 1). Subsequent co-staining of Wnt10a with Wnt family members TCF3/4 and Axin1 (rows 2 and 3, respectively; orange in color) demonstrated expression within the regenerating portion of the urothelium of all donor samples. Native urothelium directly adjacent to regenerating urothelium was devoid of Wnt10a based upon antibody staining CTNNB1 and FZD5 (a receptor for Wnt ligands) were also detected on analyzed urothelium (rows 4 and 5, respectively). The addition of CD34$^+$ HSPCs resulted in a greater degree of Wnt10a based urothelium regeneration although urothelium was still tenuous in nature (row 1, Panel B). Staining with the aforementioned Wnt family members found in Panel A demonstrated similar expression and distribution of these proteins within the urothelium. Lastly, the combination of MSC/CD34$^+$ HSPC seeded POC scaffolds (Panel C) with analogous samples demonstrate optimal urothelium growth as early as 4 weeks post-augmentation in regenerating bladder tissue accompanied by strong upregulation of Wnt10a expression (row 1). The early onset of the protective urothelial lining in the MSC/CD34$^+$ HSPC groups may have also provided an environment conducive to the superior muscle and vascular growth as demonstrated in FIGS. 2 and 3. Further staining of tissues with antibodies directed against Wnt proteins revealed multiple pathway regulators found downstream of Wnt ligand signaling (rows 2-5). The choice to select the aforementioned protein partners of Wnt10a [TCF3/4, Axin1, CTNNB1 (β-catenin), and the FZD5] was based upon laser capture microdissection of urothelium in MSC, CD34$^+$, or MSC/CD34$^+$ seeded scaffolds that were initially Wnt10a$^+$ by immunostaining This was followed by quantitative PCR against a Wnt signaling family based PCR array (Qiagen). Several other Wnt family members were found to be upregulated in the urothelium by PCR including CCND2, rac1, SFRP2, PORCN, and BTRC. Light gray arrows indicate the lumen of the bladder. All samples are 4 weeks post-augmentation. Scale Bar-50 µm.
Figure 12:
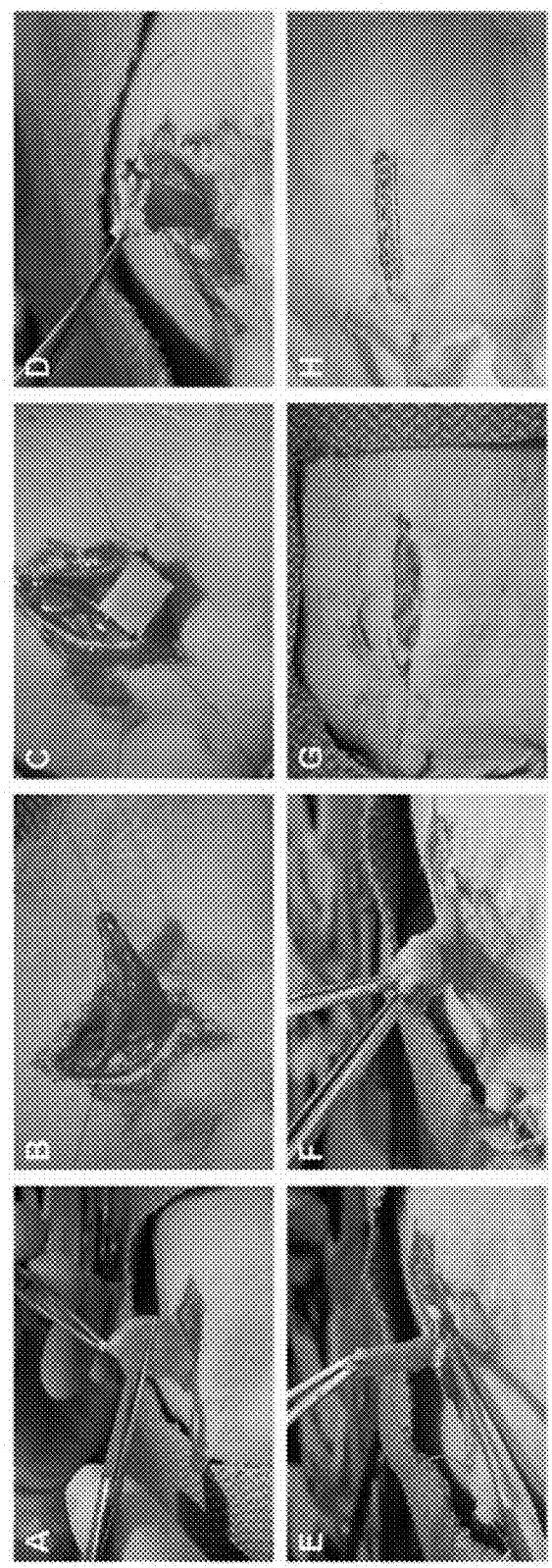
FIG. 12 shows bladder augmentation procedure. A nude rat bladder augmentation animal model was utilized (A) Following pre-operative procedures and anesthetization, a ~50% bladder cystectomy was performed with removal of the bladder dome. (B) Stay sutures were put into place at the 9:00 and 3:00 positions in order to stabilize and orient the bladder. (C-D) The bladder defect was capped with POC (+/− cells) followed by suturing along the perimeter of the POC with attachment to the freshly excised underlying bladder tissue in a watertight fashion. (E-F) Rat omentum was gently draped over surgically repaired bladder and subsequently sutured in place. (G-H) The abdominal wall was then closed with a running suture and the skin was closed with 9 mm autoclips.

Proper anatomical configuration of the bladder smooth muscle microstructure is imperative for overall bladder function since this feature in part governs repetitive contractile/relaxatory cycles that allow for proper micturition. The transplantation of SB derived BM MSCs to act as a surrogate cell source for bladder smooth muscle cells in form and function appeared to provide the cellular mimicry to recapitulate the smooth muscle layer in a bladder augmentation model. Since MSCs are known to express a variety of functional nicotinic and muscarinic receptors and maintain indistinguishable physiological responses to agonist treatment as do bladder SMCs, it is contemplated that physiological responses from environmental cues aid in the facilitation of proper bladder function (refs. 14, 15; herein incorporated by reference in their entireties). The distinct formation of organized muscle tissue was evidenced by the presence of numerous well developed, muscle fascicles oriented in a longitudinal manner as typically seen in normal bladder anatomy (ref 16; herein incorporated by reference in its entirety) This structural integrity of muscle fascicles was substantiated at the cellular level by the affirmation of key contractile bladder smooth muscle proteins in the grafted areas with no qualitative difference in expression detected between the three different donor populations. The establishment of the MSC derived muscle layer provided the subsequent foundation for the full formation of the bladder tri-layer architecture consisting of muscle, serosa, and urothelium with histological appearance approaching that of normal human bladder tissue (refs. 12, 17; herein incorporated by reference in its entirety). MSC/CD34+ constructs showed robust urothelium growth several cells in thickness within grafted areas while analogous CD34+ grafts demonstrated a moderate level of urothelial growth. MSC grafts were by far the worst and demonstrated a thin and fragile appearing urothelium along with disorganized muscle content (FIG. 11A). The combination of MSC/CD34+ HSPCs have provided specific cues to coax quiescent urothelial stem cells to exit the $G_o$ phase of the cell cycle and further potentiate regeneration of the bladder urothelium through heightened upregulation of Wnt10a and members of the Wnt family of proteins (FIG. 11B). Sonic hedgehog and Wnt signaling pathways have been implicated in urothelium regeneration and in hematopoiesis of CD34+ HSPCs (18, 19; herein incorporated by reference in their entireties).

Adequate vascularization of grafted tissue has been a significant obstacle for many organ systems (refs. 20, 21; herein incorporated by reference in their entireties). Developing tissue at the center of implanted cell/scaffold composites is highly susceptible to necrosis since nutrient and gas exchange is poor or nonexistent. The application of CD34+ HSPCs provided a unique solution to overcome this dilemma by supplying an initial foundation for increased levels of potentially functional vasculature. Data from recent studies demonstrate the utility of CD34+ HSPCs as intramyocardial injections of these cells relieve symptoms of angina and promote neovascularization in preclinical models (refs. 22, 23; herein incorporated by reference in their entireties). The increase in the number of blood vessels and percent vasculature seen at 4 weeks post-augmentation in MSC/CD34+ seeded scaffolds was striking. The number of vessels/$mm^2$ within regenerated areas of these grafts was similar amongst the three donor groups and was at least 5 fold higher than in native areas, which showed vasculature level is similar to those of MSC grafts. This effect was further corroborated via the quantification of percent vasculature in regenerated tissue which was greatest for grafts that contained both MSCs and CD34+ HSPCs. The similarities with regard to vessel number and percent vasculature between SB and non-SB groups has implications not only for SB patients in need of bladder replacement, but for bladder cancer patients who are in similar predicaments.

Figure 8:
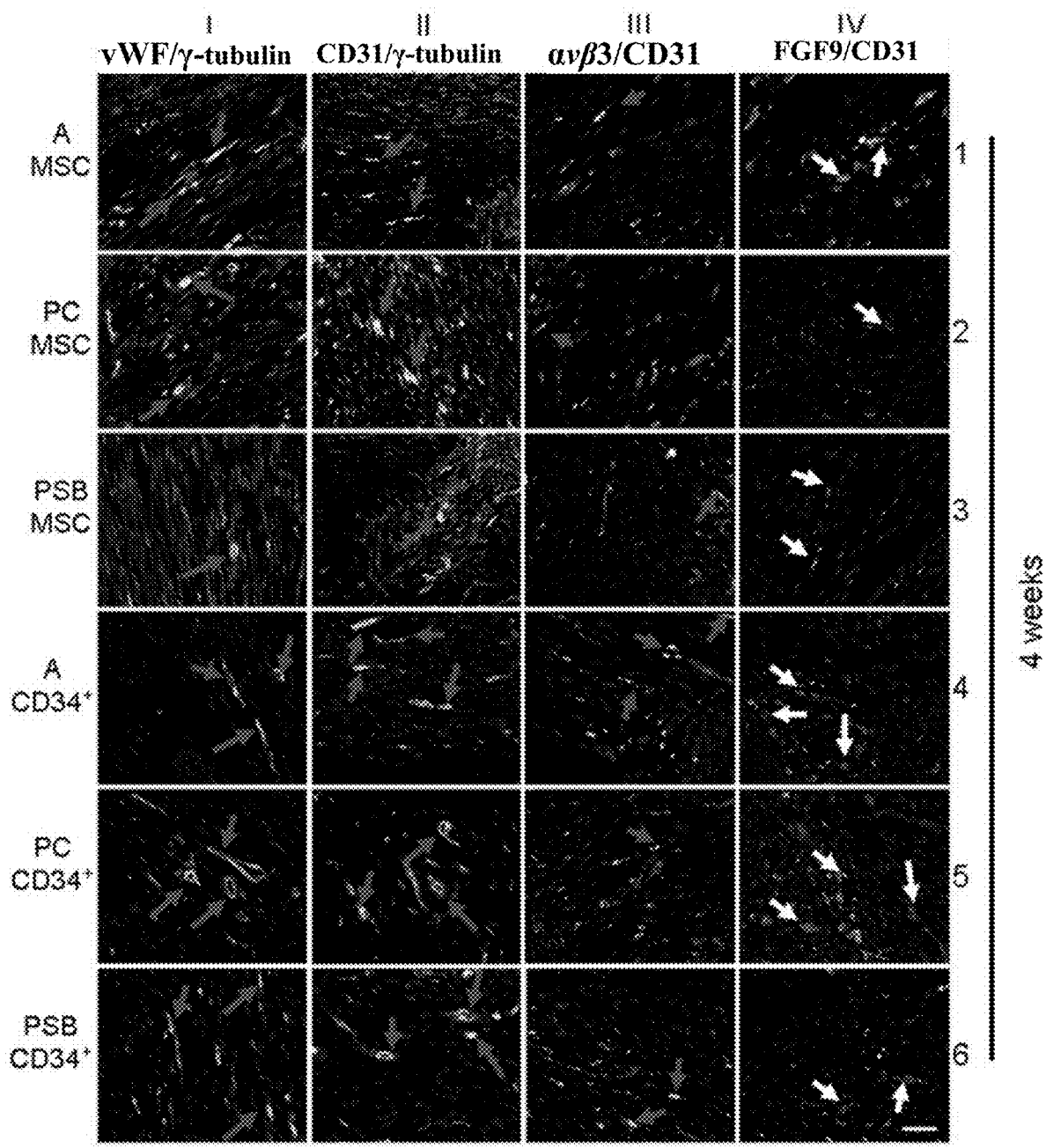
FIG. 8 shows tissue vascularization. Achieving adequate vascularization throughout engrafted tissue has been a major obstacle in tissue regeneration studies. This is particularly true at the core of grafts where gas/nutrient exchange is especially poor. Independent seeding of MSCs or CD34+ HSPCs to scaffolds provided an increase in vasculature compared to unseeded scaffolds (at 4 weeks) although the addition of CD34+ HSPCs provided an even greater degree of vasculature per area (vessels/mm$^2$) and overall percent vasculature. The best results with regard to vasculature growth were demonstrated with MSC/CD34+ HSPCs seeded scaffolds (see FIG. 3B, C, respectively). Quantitative data was substantiated by co-immunostaining with established vascular endothelial cell markers (vWF and CD31) along with human reactive γ-tubulin. vWF+/γ-tubulin+ vasculature in all donor cell seeded samples is indicated by yellow-orange co-staining (column I). This was verified with a second vascular endothelial cell marker, CD31 (column II). Under both circumstances, co-immunostaining with γ-tubulin indicated that the vasculature contained human cells. Lastly, the extent of FGF9 staining was greatly diminished in MSC or CD34+ HSPC seeded scaffolds which are in complete contrast to MSC/CD34+ HSPC seeded scaffolds that demonstrated vigorous FGF9 staining adjacent to muscle bundles and vasculature. Dark and light arrows denote vasculature. Images are counterstained with DAPI (blue) in order to visualize cell nuclei. Scale bar-50 μm

The composition of angiogenic vessels in experiments conducted during development of embodiments of the present invention was composed in part of donor MSCs and CD34+ HSPCs. Data demonstrate that these cell populations were indeed incorporated within the walls of blood vessels and were of human origin through antibody staining (FIG. 8). These findings may be attributed to one of several physiological phenomena, although the present invention is not limited to any particular mechanism of action and an understanding of the mechanism of action is not necessary to practice the present invention. These include the direct incorporation of MSCs or CD34+ HSPCs into the vessel wall at the onset of the neovascularization program or MSCs' traversal of tissue into nearby vessels as pericyte cells providing the structural support to endothelial cells that line the walls of blood vessels. Bexell et al demonstrate the ability of grafted BM MSCs to integrate into tumor vessel walls and express markers affiliated with pericytes (ref. 24; herein incorporated by reference in its entirety). Other studies indicate the likelihood of neo-vascularization because CD34+ HSPCs have demonstrated the ability to promote neo-vascularization (refs. 25, 26; herein incorporated by reference in its entirety). Additional evidence supporting the possibility that vessels found within the regenerated areas of MSC/CD34+ truly underwent angiogenesis is the coexpression of αvβ3 and CD31 in newly sprouted blood vessels. It has been established that the integrin αvβ3 is expressed on cells within vessels undergoing angiogenesis and is the target of many anti-cancer therapeutics aimed at targeting αvβ3 based angiogenesis (ref 27; herein incorporated by reference in its entirety). Lastly, the expression of FGF9 in areas of regeneration and angiogenesis has great significance as to whether the formation of endothelial sprouts is subsequently followed by their incorporation into vasoactive blood vessels. The expression of FGF9 has been shown to be highly upregulated as human smooth muscle cells assemble themselves into layered cords which are indicative of their functional capabilities. This expression of FGF9 is also evident in PSB grafts and encompasses MSC derived muscle bundles. Based on studies by Frontini et al, it is suggestive that the MSC/CD34+ grafts contain microvessels that formed in the presence of FGF9 and are vasoactive (ref 28; herein incorporated by reference in its entirety).

Figure 5:
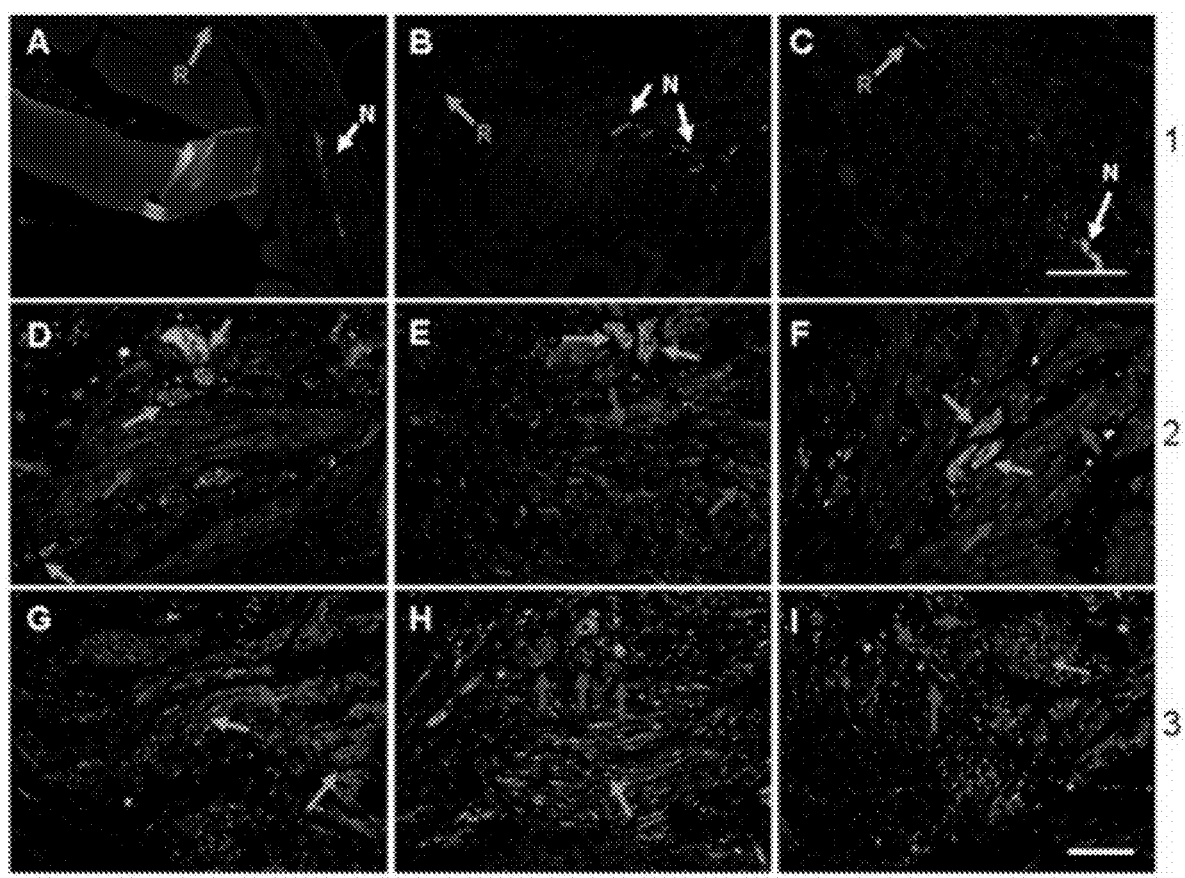
FIG. 5 shows bladder peripheral nerve regeneration. βIII tubulin neuronal expression was absent in regenerated tissue of A MSC grafts at 4 and 10 weeks, and minimal at 20 weeks (A-C, arrows: gray=regenerated tissue, white=native tissue). In contrast, regenerated tissue from MSC/CD34+ grafts at 4 weeks shows expression of βIII tubulin (D-F) and neuronal marker synaptophysin (G-I) in areas populated by grafted γ-tubulin+ cells) Fig. D and G=Adult samples; Fig. E and H=PC samples; Fig. F and I=PSB samples). Scale bar in Fig. C=250 μm. Scale bar=100 μm in remainder of image.

The difficult task of accomplishing bladder nerve regeneration following augmentation cystoplasty has been a major obstacle within the field of bladder tissue engineering. Recent studies have described the controversial use of specific surgical approaches to create artificial somatic-autonomic reflex pathways involving the bladder of patients with spinal cord injuries (ref. 29; herein incorporated by reference in its entirety). In experiments conducted during development of embodiments of the present invention, the ingrowth of peripheral nerves has been achieved as early as 4 weeks post augmentation from native tissue into areas of regenerated tissue seeded with MSC/CD34+ HSPCs, as demonstrated solely with neuronal specific antibody staining CD34+ grafts demonstrate the commencement of early nerve growth while grafts lacking the CD34+ HSPC component do not display peripheral nerve growth at 4 or 10 weeks. Regenerated peripheral nerves were located throughout the graft including the core and appear as clusters which are interspersed amongst newly formed muscle bundles comprised of MSCs (FIG. 5). It is contemplated that the increased number of blood vessels in MSC/CD34+ grafts expedited the growth and development of peripheral nerves by providing key nerve promoting factors; although the present invention is not limited to any particular mechanism of action and an understanding of the mechanism of action is not necessary to practice the present invention. CD34+ HSPCs have also been shown to express a variety of neural proteins with an overlap of hematopoietic and neuropoietic molecular signatures including nerve growth factor, its receptor TrkA, dopamine receptors DR3 and DR5, and also possess the ability to transdifferentiate into cells of neural lineage (refs. 30-33; herein incorporated by reference in their entireties). Dopamine has been determined to be a key molecule in neurite outgrowth and its interaction with CD34+ HSPCs may have contributed to the peripheral nerve regeneration at the early timepoint of these experiments (ref 34; herein incorporated by reference in its entirety).

Experiments conducted during development of embodiments of the present invention demonstrated that SB MSCs and CD34+ HSPCs respond similarly to normal, adult and pediatric control counterparts under in vitro and bladder regenerative conditions. The addition of the CD34+ HSPCs to grafts containing donor matched SB MSCs in the case of PC and PSB samples demonstrated remarkable vessel and urothelium growth in areas of regeneration. The combination of MSCs and CD34+ HSPCs provided a pro-neural growth environment that allowed for the ingrowth of peripheral nerves into areas of bladder regeneration at only 4 weeks post-augmentation. Based upon these data, autologous sources of SB derived BM MSCs in conjunction with CD34+ HSPCs may be successfully utilized as autologous surrogate cell sources to regenerate various aspects of the urinary bladder.

In some embodiments, isolated populations of mesenchymal stem cells are provided herein. In some embodiments, MSCs are derived from bone marrow or any other suitable source (e.g., isolated from tissue, derived from cell culture, etc.). In some embodiments, MSC populations used in embodiments described herein are positive for one or more (e.g., 1, 2, 3, 4, 5, or 6) of: CD29, CD44, CD73, CD90, CD105, and/or CD166; and/or negative for one or more (e.g., 1, 2, 3, 4, or 5) of: CD14, CD34, CD45, CD117, and/or CD133. In some embodiments, MSCs are CD29+, CD44+, CD73+, CD90+, CD105+, CD166+, CD14−, CD34−, CD45−, CD117−, and CD133−. In some embodiments, MSCs are isolated from cell culture or from an in vivo sample (e.g., tissue (e.g., bone marrow), etc.) based on one or more (e.g., all) of the above listed markers.

In some embodiments, isolated populations of hematopoietic stem/progenitor cells are provided herein. In some embodiments, HSPCs are derived from tissue or any other suitable source (e.g., derived from cell culture, etc.). In some embodiments, HSPC populations used in embodiments described herein are CD34 positive (CD34+). In some embodiments, HSPCs are isolated from cell culture or from an in vivo sample (e.g., tissue, etc.) based on the presence of at least the CD34 marker.

In some embodiments, the cell populations utilized in the co-transplantation methods described herein are highly specific. For example, in some embodiments MSCs exhibiting the desired markers are isolated away from other MSCs. In some embodiments, only the desired MSCs are utilized, yielding improved results over more general techniques. In some embodiments, for example, utilizing CD34+ HSPCs produces improved results over other stem/progenitor cells. In some embodiments, the results realized through the use of tailored cell populations are not inherent to more mixed, less specific populations. In some embodiments, cell populations exhibit less than 10% (e.g., <5%, <2%, <1%, <0.5%, <0.2%<, <0.1%, etc.) of the non-desired cell type (e.g., MSCs with non-desired markers (e.g., CD29−, CD44−, CD73−, CD90−, CD105ˡ, CD166−, CD14+, CD34+, CD45+, CD117+, and/or CD133+) or HSPCs with non-desired markers (e.g., CD34+).

In some embodiments, cell populations according to the invention are immunologically blinded or immunoprivileged. As used herein, "immunologically blinded" or "immunoprivileged" refers to a cell that does not elicit an immune response. As used herein, an "immune response" refers to a response made by the immune system to a foreign substance. An immune response, as used herein, includes but is not limited to transplant or graft rejection, antibody production, inflammation, and the response of antigen specific lymphocytes to antigen. An immune response is detected, for example, by determining if transplanted material has been successfully engrafted or rejected, according to methods well-known in the art. In some embodiments, an "immunogically blinded stem cell" or an "immunoprivileged stem cell" according to the invention can be allografted or xenografted without transplant rejection, and is recognized as self in the transplant recipient or host.

In some embodiments "isolating" a cell or cell population refers to the process of removing cells from an organism or tissue sample and separating away other cells which are not the desired cell type. For example, an isolated BM MSC population will be generally free from contamination by other cell types and will generally have the capability of propagation and differentiation to produce mature cells of the tissue from which it was isolated. However, when dealing with a collection of stem cells, e.g., a culture of stem cells, it is understood that it is practically impossible to obtain a collection of stem cells which is 100% pure. Therefore, an isolated stem cell can exist in the presence of a small fraction of other cell types which do not interfere with the utilization of the stem cell for analysis or production of other, differentiated cell types. Isolated stem cells will generally be at least 30%, 40%, 50%, 60%, 70%, 80%, 85%, 90%, 95%, 98%, or 99% pure. Preferably, isolated stem cells according to the invention will be at least 98% or at least 99% pure.

In some embodiments, cells are isolated by any suitable techniques (e.g., flow cytometry, fluorescence-activated cell sorting (FACS), etc.). In some embodiments, fluorescence is utilized in cell sorting to isolate the desired cell populations. Any suitable means of detecting the fluorescently labeled cells can be used. The cells may be identified using epifluorescence optics, and can be physically picked up and brought together by Laser Tweezers (Cell Robotics Inc., Albuquerque, N. Mex.). They can be separated in bulk through FACS.

A stem cell (e.g., BM MSC), progenitor cell (e.g., HSPC), or differentiated cell is "transplanted" or "introduced" into a mammal (e.g. human or non-human subject) when it is transferred from a culture vessel into a patient. In some embodiments, transplantation includes the steps of isolating a stem cell according to the invention and transferring the stem cell into a mammal or a patient. In some embodiments, isolation, culturing, and transplantation are separate steps. In some embodiments, transplantation involves transferring a stem cell population into a mammal or a patient by injection of a cell suspension into the mammal or patient, surgical implantation of a cell mass into a tissue or organ of the mammal or patient, or perfusion of a tissue or organ with a cell suspension. The route of transferring the stem cell or transplantation will be determined by the need for the cell to reside in a particular tissue or organ and by the ability of the cell to find and be retained by the desired target tissue or organ. In the case where a transplanted cell is to reside in a particular location, it can be surgically placed into a tissue or organ or simply injected into the bloodstream if the cell has the capability to migrate to the desired target organ.

The present invention is not limited by the type of scaffold. For example, a scaffold may comprise structural proteins (e.g., collagen, gelatin, etc.), carbohydrates or polysaccharides (e.g., cellulose, dextran, alginate, and chitosan), polymers (e.g., polyamide, polyester, polystyrene, polypropylene, polyacrylate, polyvinyl, polycarbonate, polytetrafluoroethylene, dextran, etc.), fibers (e.g., cotton), foams, or nitrocellulose compounds. In some embodiments, the scaffold comprises a web, matrix, and or thin film. In some embodiments, a scaffold is a 2D or 3D scaffold. In some embodiments, a scaffold provides the support for cells to proliferate and maintain their capacity to differentiate. In some embodiments, a matrix comprises one or more biodegradable elastomers. In some embodiments, a matrix comprises one or more poly(diol citrates) (e.g. Poly(1,8 octanediol-co-citrate) (POC), poly(1,6-hexanediol-co-citrate) (PHC), poly(1,10-decanediol-co-citrate) (PDC), poly(1,12-dodecanediol-co-citrate) (PDDC), poly(1,8-octanediol-co-citrate-co-MDEA) (POCM10%), poly(1,12-dodecanediol-co-citrate-co-MDEA) (PDDCM10%), etc.). In some embodiments, the present invention provides a scaffold comprising POC. In some embodiments, POC is configured to form a thin film scaffold. In some embodiments, POC provides a flexible, biodegradable, non-toxic, and/or sutural thin-film scaffold. In some embodiments, POC exhibits the capacity to function as a useful scaffold in both in vivo and in vitro settings. In some embodiments, a POC scaffold is transplantable with a desired cell mixture. In some embodiments, a scaffold (e.g. POC scaffold) provides a substrate upon which to transplant a desired cell mixture. In some embodiments, a scaffold (e.g. POC scaffold) provides a growth surface and/or material for a desired cell mixture upon transplantation. In some embodiments, a scaffold (e.g. POC scaffold) is configured to remain as part of new tissue (e.g. bladder tissue) following transplant. In some embodiments, a scaffold (e.g. POC scaffold) is configured to remain associated with transplanted cells and/or regenerated tissue (e.g. bladder tissue). In some embodiments, a scaffold (e.g. POC scaffold) is configured to degrade following transplantation (e.g. hours after transplantation, days after transplantation, weeks after transplantation, months after transplantation, years after transplantation, etc.). In some embodiments, a scaffold (e.g. POC scaffold) is configured to degrade following tissue regeneration (e.g. hours after transplantation, days after transplantation, weeks after transplantation, months after transplantation, years after transplantation, etc.).

Certain methods for isolation and co-administration of MSCs and EPCs are described, for example, in U.S. patent application Ser. No. 12/816,780; herein incorporated by reference in its entirety.

The present invention is not limited to the treatment of any particular condition or to the regeneration of any particular class of cells or tissue. In some embodiments, methods of bladder regeneration are provided; however, the cells, scaffolds, and methods described herein find use in regeneration of other tissues as well (e.g., heart, cartilage, etc.). Embodiments of the invention have been described in connection with SB, but the invention is not so limited.

Interstitial cystitis/Painful Bladder Syndrome (IC/PBS) is a state in which there is chronic pain and discomfort of the bladder and surrounding pelvic region due to unknown causes at this time. In some embodiments, diseased bladder tissue is removed and replaced with bone marrow derived populations of MSCs and CD34+ HSPCs (e.g., along with an appropriate scaffold).

EXPERIMENTAL

Example 1

Bone Marrow Cell Isolation

Pediatric BM (~1.5-5 mL/donor) was aspirated from the posterior iliac crests, pelvis, or femora of male and female SB or normal donors (n=4 each; 10-17 years of age; normal=non-diseased) undergoing orthopedic procedures. Three donor samples from each group were used for MSC augmentations, one of the three was used for MSC/CD34+ augmentations and an additional sample from each group was utilized for CD34+ augmentations. Heparinized marrow aspirates were diluted 1:4 with Dulbecco's phosphate-buffered saline (DPBS) Ca2+- and Mg2+-free (Invitrogen). Diluted marrow was underlaid with Ficoll-Paque (GE Healthcare) and centrifuged at 800 g for 30 minutes at 20° C. after which the mononuclear cell fraction was collected. Target cells were isolated via FACS with: CD29-APC (allophycocyanin); CD44– PerCP/Cy5.5 (peridinin chlorophyll protein/cyanine 5.5); CD105-FITC (fluorescein isothiocyanate); CD166-PE (phycoerythrin); CD14-Pacific Blue; CD34-PE/Cy7 (phycoerythrin/cyanine 7); CD45-APC/Cy7 (allophycocyanin/cyanine 7) (antibodies from BD Biosciences, San Diego; BD Pharmingen, San Diego; Abcam, M A; or eBioscience, San Diego) to obtain CD29+/CD44+/CD105+/CD166+/CD34-/CD45-/CD14- MSCs. The MSCs were collected and plated into Mesenchymal Stem Cell Growth Media (MSCGM; Lonza) for 7-10 days at 370 C, 5% CO2 in air. BM was also incubated with the aforementioned anti-CD34 antibody in order to isolate CD34+ HSPCs via FACS. Isolated MSCs and CD34+ HSPCs were utilized for scaffold seeding in a donor-matched setting, where appropriate. Adult MSCs and CD34+ HSPCs were purchased from Lonza. This study was approved by the Institutional Review Board at the Ann & Robert H. Lurie Children's Hospital of Chicago.

In Vitro Differentiation of Mesenchymal Stem Cells.

MSCs underwent coerced terminal differentiation into osteoblasts, adipocytes, and chondrocytes. MSC differentiation into osteoblasts was accomplished using the Mesenchymal Stem Cell Osteogenesis Kit (Millipore, MA). As per manufacturer's instructions, 24-well plates were coated with 500 μl of a 12 μg/ml vitronectin and collagen mixture and allowed to incubate for 16 hours at room temperature (RT). Following incubation the solution was removed and washed once with DPBS. MSCs were then plated at a density of 60,000 cells/well in the aforementioned coated plates with 1 mL of MSCGM and incubated overnight at 370 C with 5% CO2 in air resulting in wells that were 100% confluent the following day. MSCGM was removed and replaced with osteogenesis induction medium [DMEM-low glucose, 10% heat inactivated fetal bovine serum, 0.1 μM dexamethasone solution, 0.2 mM ascorbic acid 2-phosphate solution, 10 mM glycerol 2-phosphate solution, L-glutamine, and penicillin and streptomycin]. Media was replaced every 2-3 days with fresh osteogenesis induction media for 17 days. MSCs undergoing osteogenic induction were fixed with 70% ethanol for 1 hour at RT. After solution removal, wells were washed twice with 500 μl of water and subsequently stained with Alizarin Red S Solution (Millipore) at RT for 30 minutes. The Alizarin Red S Solution was removed and the wells were washed four times with water then imaged. Alizarin Red S was utilized to visualize calcium deposits in osteoblasts. MSC adipogenic differentiation was performed with the plating of 40,000 cells/well in a 24 well plate with 1 mL of MSCGM. Cells were incubated at 370 C with 5% CO2 in air for 5 days. Five days post-plating, MSCs were 100% confluent and underwent three cycles of an induction/maintenance protocol utilizing Adipogenic Induction Media (AIM; Lonza Inc.). Cells were induced for 3 days with the aforementioned AIM followed by 1-3 days of Adipogenic Maintenance Media (AMM; Lonza Inc.). Following three complete cycles of induction/maintenance, MSCs were cultured in AMM for 7 days, with media replacement every 2-3 days. MSCs were then fixed with 4% paraformaldehyde for 40 min at RT, and sequentially washed with DPBS then water. One ml of Oil Red 0 solution (Millipore) was added to wells and allowed to incubate at RT for 50 minutes. The Oil Red 0 solution was then removed and wells were washed three times with water and used to identify lipids within differentiated adipocytes. Chondrocyte differentiation of donor MSCs was accomplished using Mesenchymal Stem Cell Chondrogenesis Differentiation Kit (Invitrogen Cell Culture). Micromass cultures were generated by seeding 5 μl droplets containing 1.6×107 viable cells/ml. Micromass cultures were then cultivated for 2 hours at 370 C with 5% CO2 in air. Following incubation, warmed chondrogenesis differentiation media (1 g/L D-Glucose, 110 mg/L sodium pyruvate, gentamicin 5 ug/mL, L-glutamine 2 mM and chondrogenesis supplement) was added. Media was replaced every 2-3 days with fresh Chondrogenesis Induction Medium for 14 days. After 14 days of differentiation with chondrogenesis induction medium, chondrocytes were then fixed with 10% buffered formalin for 2 hours at RT. Chondrocytes were then embedded in paraffin with using a graded ethanol series and then sectioned onto glass slides. Tissue sections were then deparaffinized and then rehydrated with deionized water. Tissue sections were then stained with 1% Alcian blue solution prepared in 0.1NHCl for 30 minutes. Following a rinse with deionized water, tissue sections were stained with hematoxylin for 5 min and washed again in deionized water. Samples were then dried and mounted with Permaslip (Alban Scientific Inc., MO). Sample images (1024×768, bit depth 24) were captured using a Nikon Eclipse 50i Microscope (Nikon Inc.) Blue staining indicated synthesis of proteoglycans by chondrocytes. Images were captured utilizing a Leica DM IL light microscope equipped with Hoffman objectives, a Leica DFC295 digital color camera, and Leica software application suite (Leica, Inc., IL).

In Vitro Proliferation Assay.

MSCs were plated in 96-well plates (3,000 cells/well) followed by 18 hours of serum deprivation then grown in MSCGM for up to 17 days. At D1, D3, D5, D7, D10, D12, D14 and D17, media was removed and plates were transferred to −80° C. until a CyQuant Cell Proliferation Assay (Molecular Probes) was performed as previously described. Additional MSC-seeded plates provided standards to convert fluorescence intensity values into cell number estimates. A mean estimated cell number was calculated from 12 wells for each sample at each timepoint. Values were log-transformed for statistical analysis. Fluorescence was measured at 480/520 nm excitation/emission using a Spectramax M5 (Molecular Devices).

Oligonucleotide Genechip Microarray.

MSCs from A, PC, and PSB were utilized for total RNA isolation using the RNeasy Kit (Qiagen). RNA quality was assessed utilizing the Agilent 2100 Bioanalyzer (Agilent Technologies). Standard cDNA synthesis and subsequent hybridizations to Human Genome U133 Plus 2 microarrays (Affymetrix) were performed by The Center for Applied Genomics (The Hospital for Sick Children, Ontario, Canada) per facility's protocol. Expression data were extracted using the Robust Multi-array Averaging (RMA) method implemented in the BRB Array tool V4.2.1, from NCBI. The probe set summaries were computed utilizing a three step approach that uses a background correction on the PM data (Perfect Match), then applies quantile normalization and finally summarizes the probe set information by using Tukey's median polish algorithm. Differentially expressed genes were identified by utilizing a random-variance t-test which considers within class variation without assuming equal variance. Genes were considered statistically significant if p<0.01. A global test of whether the expression profiles differed between the classes by permuting the labels of which arrays corresponded to which classes were also used and for each permutation, the p values were re-computed and the number of genes significant at the 0.01 level was noted.

MSC Immunophenotyping.

Flow cytometric analyses of donor MSCs was performed on a BD LSR Fortessa (Becton Dickinson), preceded by staining with the aforementioned fluorochrome conjugated antibodies and CD73-PE, CD90-FITC, CD117-FITC and CD133-PE. Approximately 20,000 gated events were collected for data analysis and plots show labeled and non-labeled cells at fluorochrome-appropriate settings.

poly(1,8-octanediol-co-citrate) (POC) Scaffold Synthesis

POC scaffold synthesis was accomplished with the addition of equimolar amounts of 1,8 octanediol (Sigma Aldrich, MO) and citric acid (Sigma Aldrich) followed by the melting at 160° C. with stirring as previously described (Sharma A K, et al. (2010) Biomaterials 31:6207-6217; herein incorporated by reference in its entirety). The temperature of the solution was then slowly reduced to 140° C. for 30 minutes and subsequently cooled to create a pre-polymer. This solution was further dissolved into 100% ethanol producing a 30% w/v solution. This solution was poured into an untreated flat bottomed glass mold, transferred to a heated oven and underwent polymerization at 55° C. for 7 days. Following post-polymerization, the POC scaffolds were de-molded and unreacted monomer was removed by incubation in DMEM (Lonza Inc.) with changes every 6 hours within a 24 hour period.

POC Scaffold Seeding

Scaffolds were synthesized and mechanical testing was performed as previously described. (R2) POC scaffolds (0.50 cm×0.75 cm×0.2 cm) used for augmentation studies were seeded at $1.5 \times 10^4$ MSCs/cm2 and allowed to grow for 1 week in vitro prior to augmentation. $1-2 \times 10^5$ CD34+ HSPCs were also added to POC or POC/MSC scaffolds and allowed to attach overnight prior to bladder augmentation procedures in separate studies.

Immunocompromised Rodent Bladder Augmentation Model

Adult athymic female nude rats underwent bladder augmentation. Intraperitoneal injections of ketamine and xylazine (60 mg/kg and 5 mg/kg, respectively) were used to anesthesize all animals. An injection of the analagesic Buprenex (1 mg/kg) was administered subcutaneously to diminish any post-operative pain. A 1 cm midline abdominal incision in the vertical plane was created to expose the abdominal wall. This was followed by the physical separation of the abdominal wall which led to the identification of the urinary bladder. A 50-60% supratrigonal cystectomy was performed from anterior to posterior positions. The cystectomized defect was augmented with the POC/MSC or POC/MSC+CD34+ HSPCs. Unseeded POC scaffolds were utilized in a previous study and consistently provided results that demonstrated unseeded POC was conducive to high levels of collagen deposition. The bladder was sutured shut with 7-0 polyglactin suture in a watertight fashion and was enveloped with omentum in the area containing the POC/cell composites. The abdominal wall was then closed with 5-0 ethibond running suture and the skin closed with 9 mm autoclips. Group I [A POC/MSC, A POC/CD34+, A POC/MSC+CD34+]; Group II [PC POC/MSC, PC POC/CD34+, PC POC/MSC+CD34+]; Group III [PSB POC/MSC, PSB POC/CD34+, PSB POC/MSC+CD34+] animals were sacrificed at 4 weeks. A POC/MSC, PC POC/MSC, and PSB POC/MSC animals were sacrificed at 10 weeks. A minimum number of three BM donors were used for SB and PSB groups and one donor was used for the A group for in vivo studies. The differing number of animals utilized in each study group was dependent upon the number of cells isolated from bone marrow samples (where applicable) combined with animal mortality rates.

Histological Analysis of Augmented POC-Tissue Composites

Full thickness bladder tissue specimens were removed immediately following euthanasia of animals and were fixed in 10% buffered formalin phosphate (Fisher Scientific, IL). Samples were dehydrated through a series of graded ethanol exchanges and embedded in paraffin according to well established protocols at 4 and 10 week timepoints. Paraffin embedded bladder tissue was sectioned onto glass slides (10 μm) using a RM2125 RT Microtome (Leica) and was subsequently stained with Masson's Trichrome (Sigma-Aldrich). The slides were deparaffinized at 620 C for 5 min on a hot plate followed by treatment with xylenes, graded ethanol washes and deionized water. Slides were placed in Bouin's solution for 15, min then rinsed under running tap water. Hematoxylin staining for 5 min followed Bouin's staining and was followed by rinsing and 5 minutes of staining with Scarlet-Acid Fuchsin. Following a rinse with deionized water, slides were subjected to a mixture of phosphotungstic acid/phosphomolybdic acid stain, followed by Aniline Blue staining Lastly, a solution of 1% acetic acid was utilized as a wash. Slides were then placed in 95-100% ethanol and rinsed in xylene. After drying, a coverslip was placed over the tissue and secured with 2-3 drops of Permaslip (Alban Scientific Inc., MO).

Quantitative Evaluation of Histological Stained POC-Tissue Composites

Adult athymic female nude rats (NCI, MD; ~200-250 g) underwent bladder augmentation as described. The cystectomized defect was augmented with POC/MSC, POC/CD34+ HSPCs, POC/MSC+CD34+ HSPC, or seeded POC scaffolds. Groups I-III described above were sacrificed at 4 weeks. A POC/MSC, PC POC/MSC, and PSB POC/MSC animals were sacrificed at 10 weeks. Full thickness bladder tissue specimens were removed at their respective timepoints and underwent Masson's Trichrome (Sigma-Aldrich, MO) staining and were evaluated for muscle and collagen content by an established protocol.

Explanted bladder tissue/scaffolds which underwent Masson's Trichrome staining were evaluated for muscle and collagen content. Muscle to collagen ratios were digitally quantified using the Nikon Eclipse 50i Microscope (Nikon Inc.) and Spot Advanced Imaging Software (Diagnostic Instruments). Sample images (1600×1200 pixels, bit depth 24) were opened with Adobe Photoshop CS3 (Adobe Systems Inc.). The contrast of red pixels from blue pixels was enhanced by a two-fold elevation of magenta levels followed by a two-fold depression of cyan levels in the red and magenta spectra. This contrast was further improved by a two-fold elevation of cyan levels followed by a two-fold depression of magenta levels in the cyan and blue spectra. The selection color range tool with a fuzziness level of 115% was then used to digitally select the red or blue pixels of the entire image. Selected pixels were subsequently quantified using the image histogram tool and a muscle to collagen ratio was calculated from these values. In cases where urothelial cells, red blood cells, or debris were present, images were edited to remove these structures to preserve a more accurate representation of the muscle to collagen ratio from the red to blue ratio. Areas of regenerated tissue were subjected to an average of twelve random microscopic fields to determine muscle to collagen ratios as previously described. All data shown as percent muscle means±SE. All animal procedures were performed in accordance with guidelines set forth and approved by the Ann & Robert H. Lurie Children's Research Center Institutional Animal Care and Use Committee.

Immunofluorescent and Quantitative Analysis of Augmented Tissues Following the dehydration, embedding and de-paraffinization process as previously described, tissue samples were subjected to immunofluorescent staining Briefly, slides were subjected to antigen retrieval consisting of 15 min of boiling in citrate buffer (0.01M citrate solution, pH 6.0 with 0.05% Tween-20) and then cooled to RT for approximately 30 mins. Staining consisted of a blocking step for 15 min in bovine serum albumin (BSA, 5 mg/ml) followed by a 40 min incubation at RT with the primary antibody. After washing with DPBS, slides were incubated for 30 min with a secondary antibody and eventually rinsed with DPBS and air dried. Slides were mounted with Vectashield (Vector Laboratories). Primary antibodies utilized in this study were directed against epitopes for markers of bladder smooth muscle cells utilizing antibodies against smooth muscle γ-actin (Millipore), calponin, or caldesmon. Ki-67, human reactive γ-tubulin and elastin; CD31, αvβ3, FGF9 were also utilized (all from Santa Cruz Biotechnology Inc.) and Wnt10a and vWF (Abcam) in conjunction with either an Alexa Red 555 or FITC conjugated secondary antibody (Molecular Probes) following established protocols. The anti-neuronal antibodies βIII tubulin and synaptophysin (Covance Inc., TN; Santa Cruz Biotechnology Inc., respectively) were utilized to determine the extent of peripheral nerve growth in areas of regenerated bladder. Primary antibodies were used at dilutions from 1:100 to 1:250. Species-specific secondary antibodies were utilized at a 1:400 dilution. Immunofluorescence quantification was carried out using a Nikon Eclipse 50i Microscope (Nikon Inc.) and Spot Advanced Imaging Software (Diagnostic Instruments). The number of Ki-67+ cells was determined by manual counting through the utilization of the eraser tool within Adobe Photoshop to mark colored cells. Fluorescent images (1600×2000 pixels, bit depth 24) were opened with Adobe Photoshop CS3 (Adobe Systems Inc.). All samples were additionally stained with 4',6-diamidino-2-phenylindole (DAPI) to identify cells by nuclei visualization.

Quantification of in vivo Vessel Formation Trichrome sample images (1600×2000 pixels, bit depth 24) were opened with Adobe Photoshop CS3 (Adobe Systems Inc.) and were initially characterized utilizing a Nikon Eclipse 50i Microscope (Nikon Inc., NY) equipped with Spot Advanced Imaging Software (Diagnostic Instruments, MI). Vessel numbers were quantified utilizing the pen tool based upon images of grafts in both native and regenerated areas. Individual vessels were selected manually and subsequently quantified using the image histogram tool to acquire pixel density for each vessel. Data represented as mean number of vessels/mm$^2$ and mean percent vasculature (means±SE).

Laser Capture Microdissection and Quantitative PCR

Cell/scaffold specimens were isolated immediately following euthanasia and were fixed in 10% buffered formalin phosphate (Fisher Scientific, PA). The tissue was dehydrated through a series of graded ethanol exchanges followed by paraffin washes and placed into molds. Samples were sectioned at a thickness of 10 μm using a RM2125 RT Microtome (Leica) onto membrane slides (Zeiss, New York) and subjected to staining with Wnt10a (Abcam). Tissue containing slides were blocked for 15 min in bovine serum albumin (BSA, 5 mg/ml) followed by a 30 min incubation at room temperature with Wnt10a antibody at a 1:100 dilution. After washing with DPBS, slides were incubated for 30 min with an Alexa Red 568 secondary antibody at a 1:400 dilution. Slides were then rinsed with DPBS, and allowed to dry. Specific sections of the regenerated urothelium positive for Wnt10a expression were removed by laser capture microdissection on a Zeiss PALM Microdissection System (purchased through NCRR grant 1S10RR025624-01). Samples were collected in an AdhesiveCap (Zeiss), and then immediately taken for RNA extraction using a NucleoSpin FFPE RNA Kit (Macherey-Nagel, Germany), per manufacturer's instructions. RNA was subjected to PCR assays utilizing the WNT Signaling Pathway RT2 PCR Array (Qiagen, CA) according to manufacturer's protocol. Following analysis of PCR data, tissue sections from A, PC, and PSB samples containing either MSCs, CD34+ HSPCs, or MSC/CD34+ HSPCs were stained with antibodies against the WNT protein family members TCF3/4, Axin 1, CTNNB1, and FZD5 (FIG. 11B) in order to determine the presence of these proteins in urothelium regeneration.

Statistical Analysis

Differences between bladder augmentation groups were determined using ANOVA, with the Tukey-Kramer adjustment for multiple comparisons. Paired t-test was used for comparison of native and regenerated tissue within each group. In vitro proliferation data was analyzed using a linear mixed polynomial model with a random intercept, after logarithm transformation of repeated measurements; pairwise comparisons were conducted using the Tukey-Kramer method. $p<0.05$ was considered statistically significant. Analyses were performed using SAS 9.2 software (SAS Institute, North Carolina). Proliferation data plot generated using R Software (The R Foundation for Statistical Computing, r-project.org).

Example 2

MSC Characterization

Figure 6A:
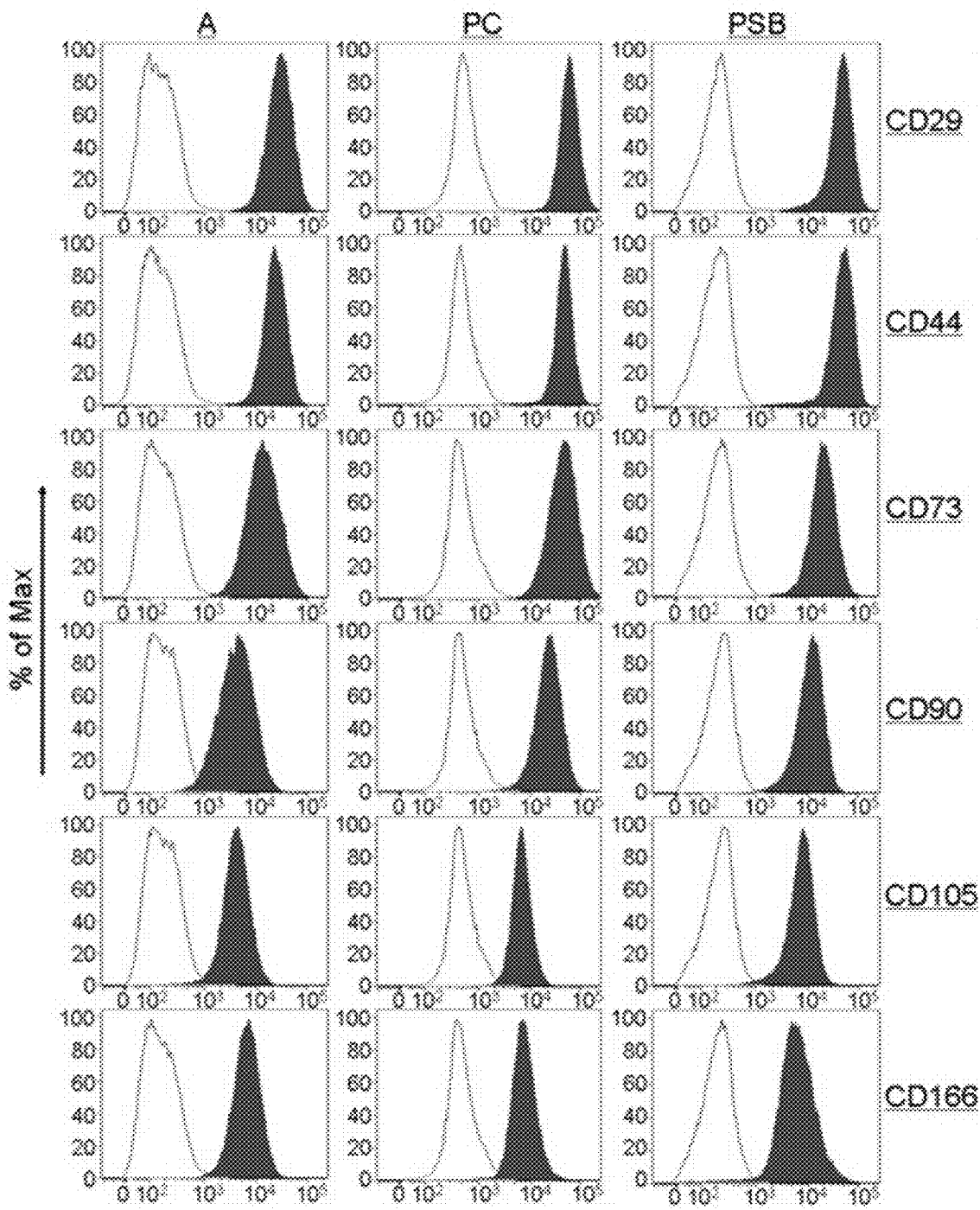
FIG. 6A-B shows MSC immunophenotyping. Immunophenotyping data of donor MSCs revealed the expression of surface markers CD29, CD44, CD73, CD90, CD105 and CD166. The expression of the hematopoietic cell lineage markers CD14, CD34, CD45, CD117, and CD133 were absent from these donor samples. Data is representative of multiple donor samples in the case of PC and PSB samples.
Figure 6B:
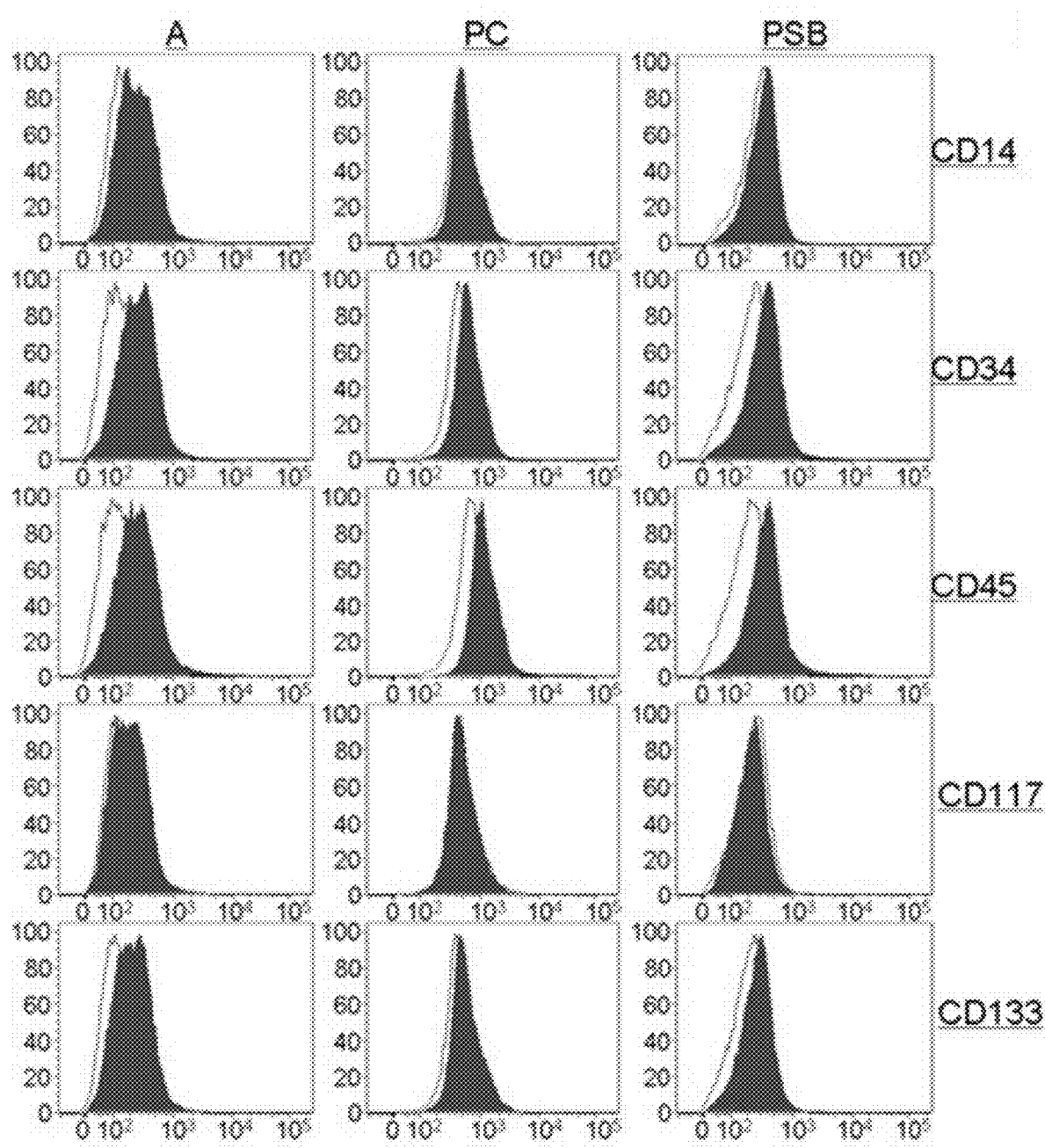
Figure 6C:
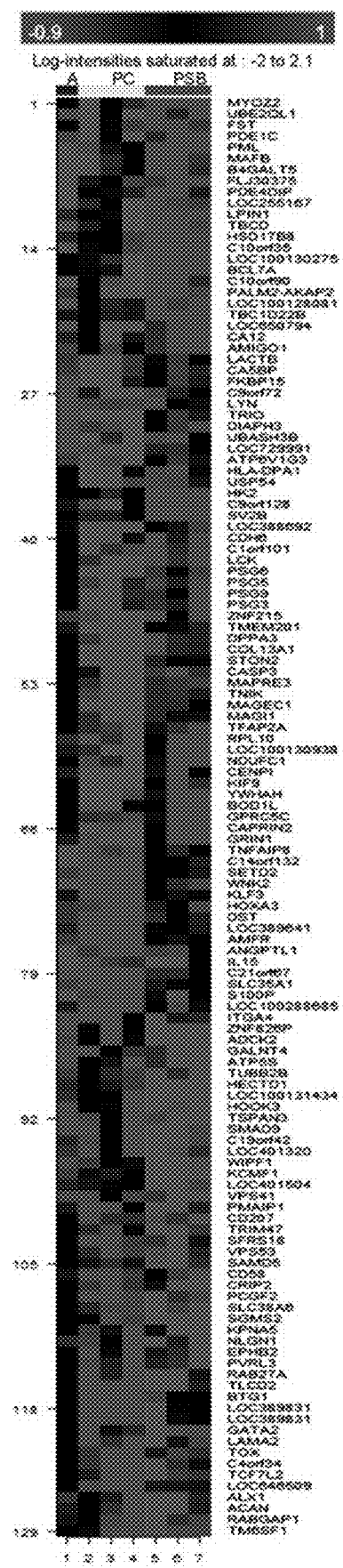
FIG. 6C shows microarray analysis of donor MSCs. Microarray analyses revealed differential expression of 129 unique genes (p<0.01) between PSB and PC samples. Data is representative of multiple donor samples in the case of PC and PSB groups [A (n=1 donor); PC (n=3 donors); PSB (n=3 donors); p<0.01].
Figure 6D:
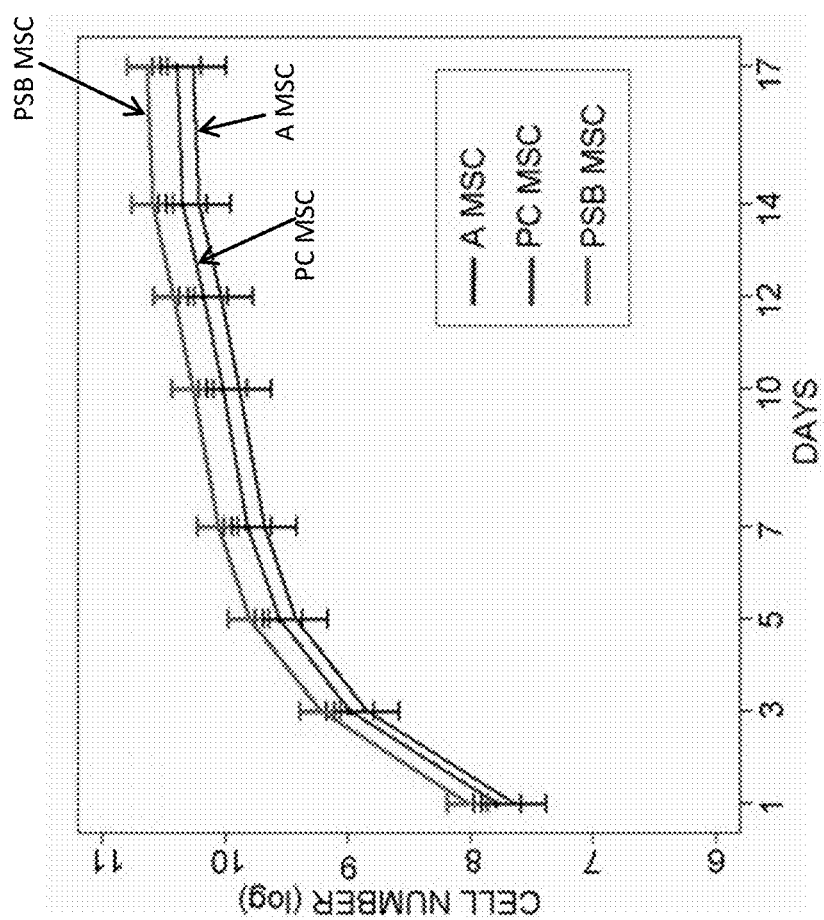
FIG. 6D shows in vitro proliferation analysis of donor MSCs. MSCs isolated from each donor group (A, PC, PSB) demonstrated a rapid growth phase from days 1-5 of culture followed by a gradual decrease in growth over the remaining duration of the experiment. However, there were no significant differences with regard to proliferative capacity between donor groups at any given timepoint. In vitro proliferation data for A, PC and PSB MSCs was analyzed using a linear mixed polynomial model with a random intercept, after logarithm transformation of repeated measurements. Pair-wised comparisons were conducted using the Tukey-Kramer method. Adjusted p-values of <0.05 were considered significant (SAS 9.2 software, SAS Institute, North Carolina). Data plot generated using R Software (The R Foundation for Statistical Computing, r-project.org).

BM MSCs isolated from A (adult), PC (pediatric control; donors 01, 13, 18), and PSB (pediatric SB, donors 02, 07, 09) samples demonstrated typical fibroblast morphology under MSC maintenance culture conditions visualized by light microscopy (FIG. 1B-D, column I) (ref 10; herein incorporated by reference in its entirety). MSCs were induced to undergo tri-lineage differentiation into osteoblasts, adipocytes, and chondrocytes. Osteoblasts were Alizarin Red S+(column II) while adipocytes were Oil Red O+(column III) and chondrocytes were Alcian blue+(column IV). Quantitative analyses of cellular differentiation demonstrated similar trends across groups (Table 1). Flow cytometric based immunophenotyping of MSCs demonstrated cellular expression of MSC surface markers CD29, CD44, CD73, CD90, CD105 and CD166 with the exclusion of hematopoietic cell lineage markers CD14, CD34, CD45, CD117, and CD133 (FIG. 6A-B). Whole-genome microarray analyses revealed differential expression of 194 genes between PSB and PC samples. 86 probe sets were up-regulated in PSB while 108 were down-regulated in PSB samples (FIG. 6C). Since certain probe sets belonged to the same genes, 129 unique genes were identified consisting of several gene ontological groups (Table 2). Lastly, in vitro proliferation assays demonstrated no statistically significant differences between groups at any timepoint (FIG. 6D).

Pathologies associated with SB did not affect MSC multipotentiality or cell surface marker expression. Microarray data further demonstrate that PC and PSB MSCs have remarkably similar molecular signatures. Adult and PC samples were utilized as control populations throughout this study.

TABLE 1

Quantification of in vitro trilineage cellular differentiation of MSC donor groups

| Group and donor | Osteoblast staining Alizarin Red S (% red) | Adipocyte staining Oil Red O (% red) | Chondrocyte staining Alcian blue (% blue) |
| --- | --- | --- | --- |
| A MSC | 14.5 ± 1.3 | 38.2 ± 3.9 | 75.2 ± 1.5 |
| PC MSC | | | |
| 01 | 15.8 ± 1.5 | 34.9 ± 1.9 | 74.4 ± 1.4 |
| 13 | 14.4 ± 1.7 | 37.7 ± 2.3 | 74.8 ± 1.4 |
| 18 | 15.6 ± 2.3 | 39.2 ± 4.6 | 72.0 ± 0.9 |
| PSB MSC | | | |
| 02 | 26.7 ± 2.3 | 38.4 ± 2.8 | 74.0 ± 1.5 |
| 07 | 16.7 ± 2.1 | 35.1 ± 1.9 | 74.8 ± 2.7 |
| 09 | 14.6 ± 1.1 | 43.3 ± 3.6 | 75.3 ± 1.2 |

The multipotential nature of donor MSCs was evaluated in vitro from all MSC donor groups as demonstrated in FIG. 1 B-D. Subsequent cellular quantification of these groups revealed similar levels of differentiation across donor groups for all lineages. Osteoblast and adipocyte stained (n = 4 images each) or chondrocyte stained (representing two micromasses; n = 10 images total) images were quantified for each donor sample. The degree of staining was quantified for each image by determining pixel counts. Red pixels indicated staining by Alizarin Red (osteoblasts) S or Oil Red O (adipocytes) and blue pixels indicated staining by Alcian blue (chondrocytes). Osteoblast and adipocyte percentages were determined by the formula (red pixels/total pixels) × 100. Chondrocyte percentages were determined by the formula (blue pixels/total pixels) × 100. Data are shown as means ± SE.

TABLE 2

Gene ontology (GO) analysis between PC and PSB MSCs
Observed in selected subset (O), Expected in selected subset (E), and Observed/Expected (O/E)

| GO ID | Go term | O | E | O/E |
| --- | --- | --- | --- | --- |
| | Cellular component | | | |
| GO: 0005604 | Basement membrane | 5 | 0.82 | 6.08 |
| GO: 0044420 | Extracellular matrix part | 7 | 1.37 | 5.11 |
| GO: 0005813 | Centrosome | 8 | 1.95 | 4.10 |
| GO: 0005874 | Microtubule | 8 | 2.39 | 3.35 |
| GO: 0005578 | Proteinaceous extracellular matrix | 8 | 3.05 | 2.63 |
| GO: 0005815 | Microtubule organizing center | 8 | 3.13 | 2.55 |
| GO: 0016604 | Nuclear body | 5 | 2.00 | 2.49 |
| GO: 0044456 | synapse part | 7 | 3.09 | 2.26 |
| | Molecular function | | | |
| GO: 0015631 | Tubulin binding | 6 | 1.06 | 5.64 |
| GO: 0005529 | Sugar binding | 5 | 1.46 | 3.42 |
| GO: 0004842 | Ubiquitin-protein ligase activity | 5 | 1.79 | 2.80 |
| GO: 0005096 | Gtpase activator activity | 6 | 2.23 | 2.69 |
| GO: 0016881 | Acid-amino acid ligase activity | 7 | 2.69 | 2.60 |
| GO: 0019787 | Small conjugating protein ligase activity | 5 | 1.94 | 2.58 |
| GO: 0030246 | Carbohydrate binding | 7 | 2.95 | 2.37 |
| GO: 0016879 | Ligase activity, forming C—N bonds | 7 | 3.04 | 2.30 |
| GO: 0005083 | Small gtpase regulator activity | 5 | 2.26 | 2.22 |
| GO: 0003779 | Actin binding | 5 | 2.47 | 2.02 |
| | Biological process | | | |
| GO: 0050773 | Regulation of dendrite development | 5 | 0.27 | 18.24 |
| GO: 0016358 | Dendrite development | 5 | 0.56 | 8.85 |
| GO: 0008629 | Induction of apoptosis by intracellular signals | 5 | 0.71 | 7.00 |
| GO: 0050769 | Positive regulation of neurogenesis | 5 | 0.73 | 6.84 |
| GO: 0010720 | Positive regulation of cell development | 6 | 0.95 | 6.33 |
| GO: 0010769 | Regulation of morphogenesis involved in differentiation | 7 | 1.24 | 5.65 |
| GO: 0022604 | Regulation of cell morphogenesis | 7 | 1.25 | 5.62 |
| GO: 0048705 | Skeletal system morphogenesis | 7 | 1.25 | 5.58 |
| GO: 0002429 | Immune response-activating cell surface receptor signaling pathway | 6 | 1.08 | 5.56 |
| GO: 0010975 | Regulation of neuron projection development | 7 | 1.26 | 5.54 |
| GO: 0002768 | Immune response-regulating cell surface receptor signaling pathway | 6 | 1.11 | 5.39 |
| GO: 0045216 | Cell-cell junction organization | 6 | 1.20 | 5.01 |
| GO: 0050851 | Antigen receptor-mediated signaling pathway | 5 | 1.01 | 4.97 |
| GO: 0031344 | Regulation of cell projection organization | 7 | 1.51 | 4.63 |

TABLE 2-continued

Gene ontology (GO) analysis between PC and PSB MSCs
Observed in selected subset (O), Expected in selected subset (E), and Observed/Expected (O/E)

| GO ID | Go term | O | E | O/E |
|---|---|---|---|---|
| GO: 0045664 | Regulation of neuron differentiation | 9 | 2.00 | 4.49 |
| GO: 0050870 | Positive regulation of T-cell activation | 7 | 1.58 | 4.43 |
| GO: 0050863 | Regulation of T-cell activation | 9 | 2.11 | 4.26 |

Histological and Morphometric Analyses of Grafts

Figure 2A:
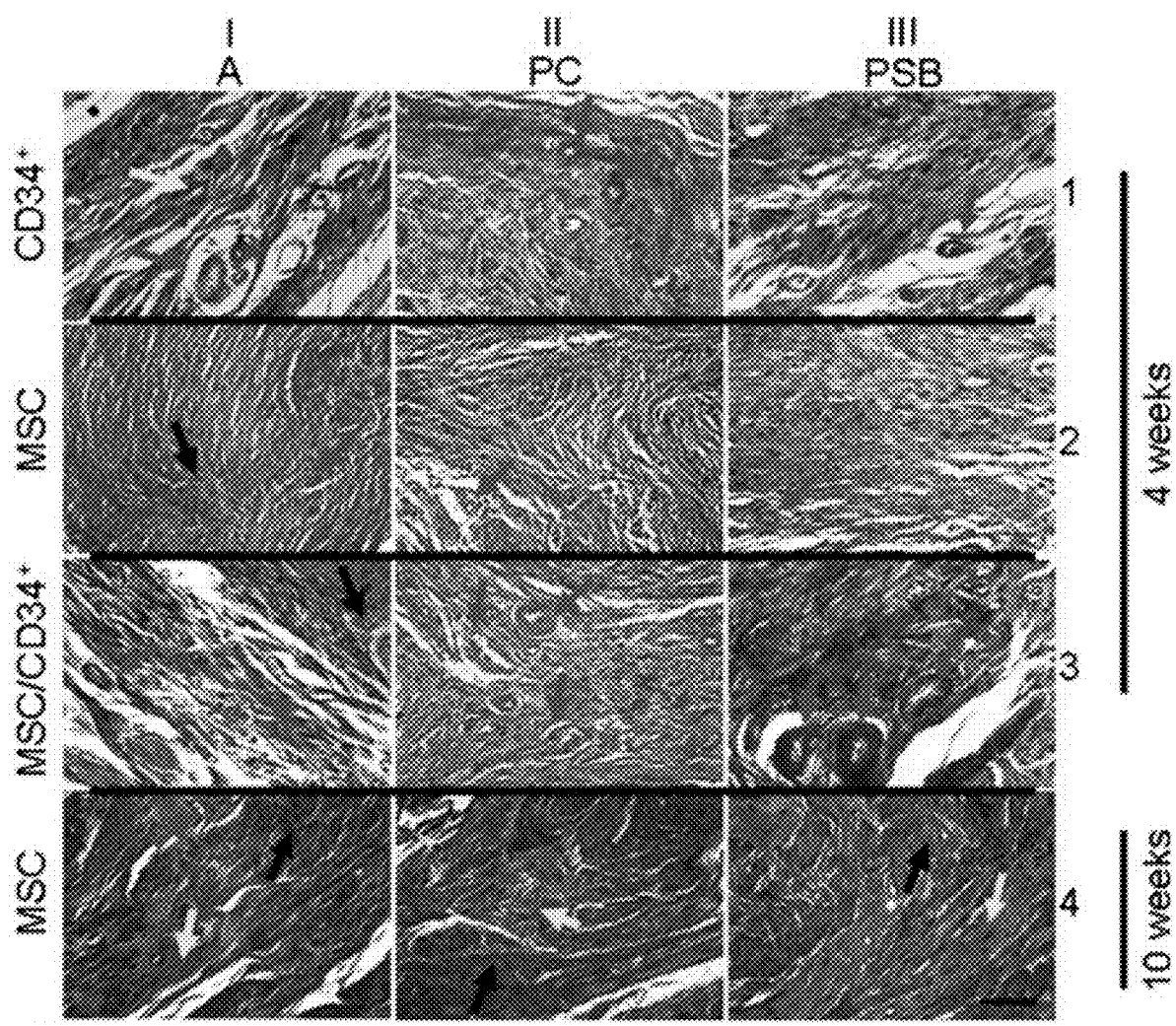
FIG. 2A-B shows effects of graft cell type and in vivo duration on regenerating musculature. (A) Regenerated tissue from MSC groups at 10 weeks post-augmentation showed well organized muscle fascicles with homogenous collagen distribution (row 4). $MSC/CD34^+$ groups demonstrated better muscle organization than MSC and $CD34^+$ groups 4 weeks post-augmentation (rows 1-3). Blood vessel distribution was also found to be greatest in $MSC/CD34^+$ groups followed by $CD34^+$ then MSC groups 4 weeks post-augmentation. Images are representative of multiple samples/animals within a group. Arrows: black=muscle, white=collagen, gray=blood vessel. 400× magnification; scale bar-50 µm (B) Significantly higher mean muscle content was observed in $MSC/CD34^+$ grafts compared to MSC and $CD34^+$ grafts 4 weeks post-augmentation. Mean percent muscle values for $MSC/CD34^+$ groups at 4 weeks were similar to those of MSC groups at 10 weeks. $CD34^+$ groups demonstrated the lowest muscle content among seeded groups. Dotted line reflects mean muscle content for an unseeded POC graft group (19.3±1.9%). Data presented as mean±SE; *$p<0.01$ **$p<0.0001$ for $MSC/CD34^+$ vs. MSC and $CD34^+$ groups (4 weeks).
Figure 2B:
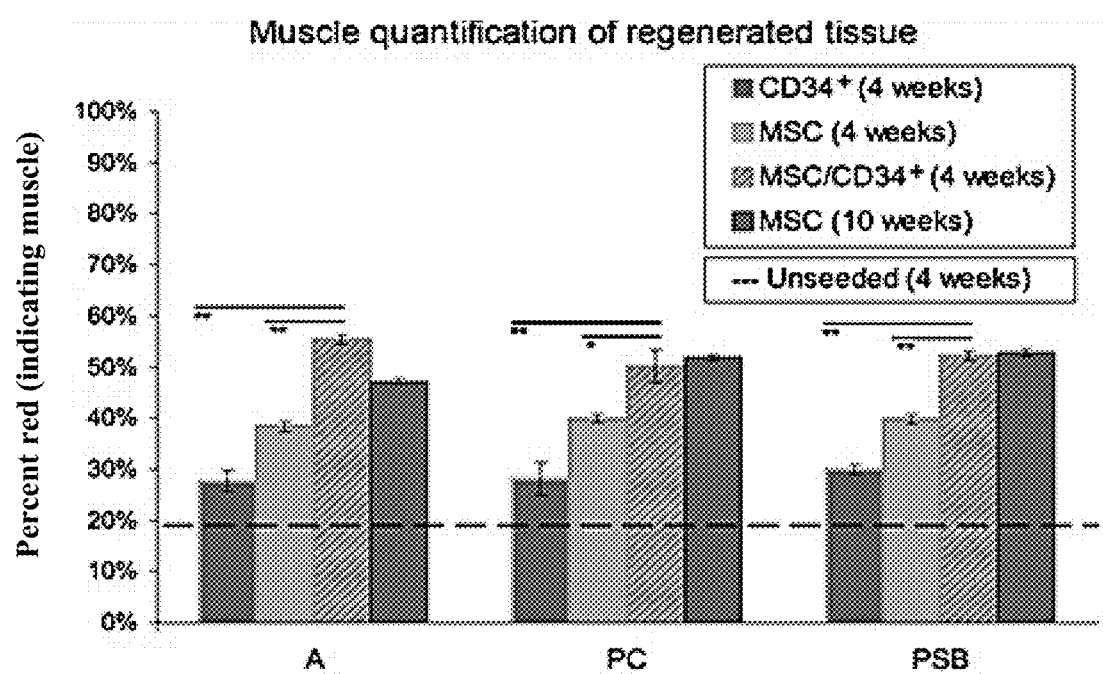

Masson's Trichrome staining of MSC seeded scaffolds 10 weeks post-augmentation (see FIG. 12A-H for surgical representation of the bladder augmentation procedure), revealed highly defined, well-organized muscle fascicles (red) interspersed with suitable levels of collagen (blue; FIG. 2A, row 4) and is consistent with normal human bladder tissue (FIG. 7A) (ref 12; herein incorporated by reference in its entirety). Varying degrees of tissue organization were observed for all groups 4 weeks post-augmentation where MSC and CD34+ groups were highly disorganized (FIG. 2A, rows 1, 2) while MSC/CD34+ groups displayed a greater propensity for tissue organization including vessel distribution (FIG. 2A, row 3). Evidence of obstruction, stricture, dilation, stone formation, calcification or diverticulum was not detected upon gross examination of the upper urinary tracts (whole bladders, ureters, and kidneys). Evidence of any necrotic bladder tissue was also lacking Muscle/collagen ratio is indicative of the level of regeneration in areas engrafted with cell-seeded scaffolds (ref. 13; herein incorporated by reference in its entirety). Previous data from analogous augmentations demonstrated that unseeded POC grafts contained ~20% muscle 4 and 10 weeks post-augmentation (ref 13; herein incorporated by reference in its entirety). Within this study, grafts from the MSC/CD34+ groups exhibited significantly higher mean muscle content than grafts from MSC and CD34+ groups 4 weeks post-augmentation (2.6-2.9× higher than unseeded scaffolds, vs. 2.0-2.1× greater and 1.4-1.6× greater, respectively). While CD34+ grafts did not attain muscle levels demonstrated by MSC/CD34+ or MSC grafts, the addition of CD34+ HSPCs to MSC grafts increased 4 week MSC/CD34+ graft muscle content to the levels of MSC groups at 10 weeks. No differences were observed with respect to donor (FIG. 2B). The distribution of blood vessels was also found to be greatest in MSC/CD34+ groups followed by CD34+ then MSC groups at the 4 week timepoint.

At 4 weeks post-augmentation, significantly higher mean muscle content was observed in MSC/CD34+ grafts as compared to MSC and CD34+ grafts (A-CD34+27.7±2.1%, PC-CD34+28.2±3.2%, PSB-CD34+30.0±1.0%; A-MSC 38.4±1.0%, PC-MSC 39.9±0.8%, PSB-MSC 39.9±0.9%; A-MSC/CD34+55.3±0.9%, PC-MSC/CD34+50.1±3.2%, PSB-MSC/CD34+52.2±1.0%); mean percent muscle values for MSC/CD34+ groups at 4 weeks were similar to those of MSC groups at 10 weeks (A-MSC 47.2±0.6%, PC-MSC 51.9±0.6%, PSB-MSC 52.8±0.7%). CD34+ groups demonstrated the lowest muscle content among seeded groups. Dotted line reflects mean muscle content for the unseeded graft group (19.3±1.9%). All grafts utilized POC scaffolds.

Blood Vessel Regeneration with MSC/CD34+Grafts

Figure 7:
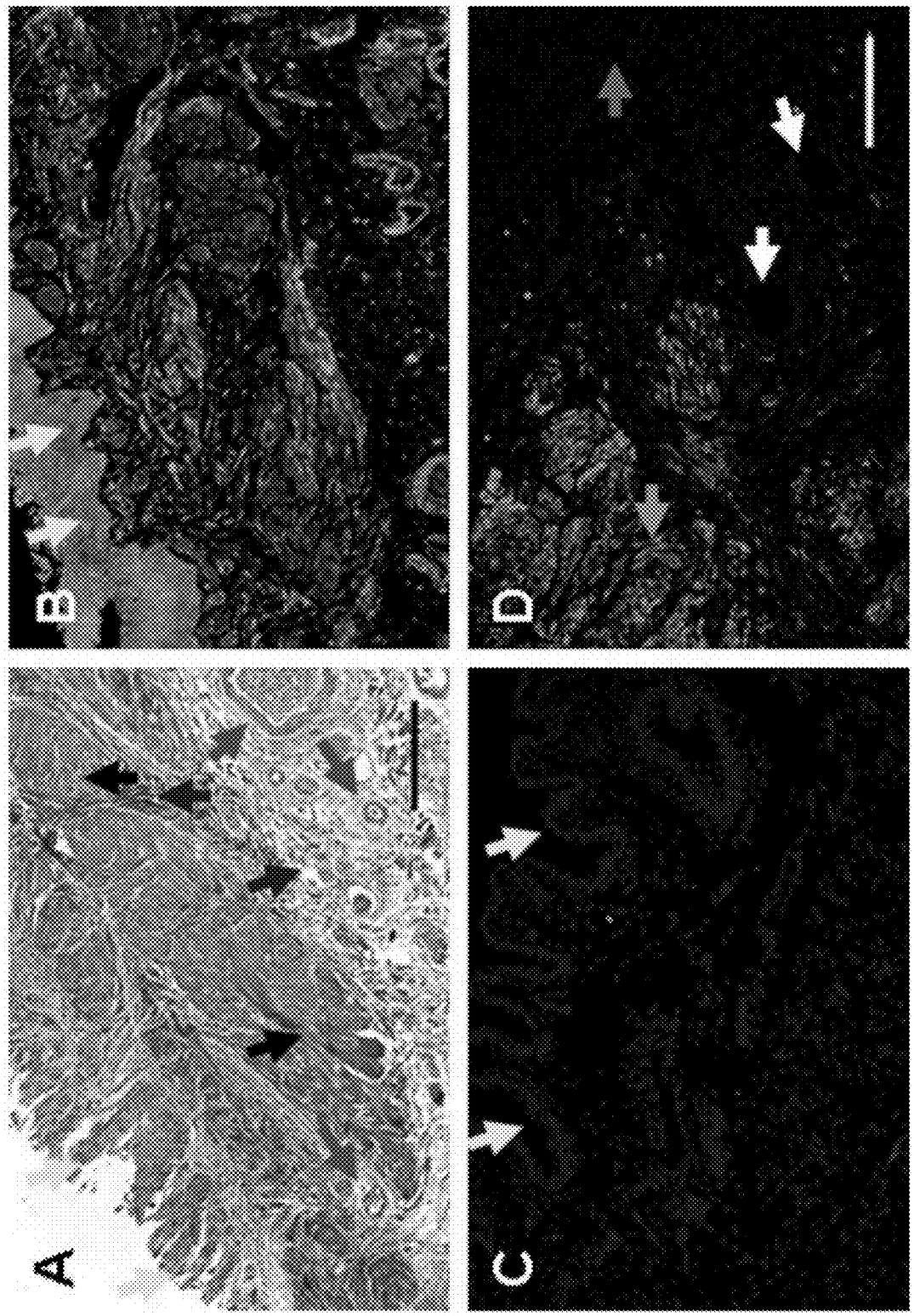
FIG. 7 shows control experiments. (A) Human bladder tissue stained with Masson's Trichrome demonstrated normal tri-layer bladder architecture and was utilized as a visual comparison to POC/cell augmented scaffolds within the context of this study. White arrows indicate the watertight urothelial cell layer (located on luminal side of the bladder) while black arrows depict highly organized muscle fascicles. Dark gray arrows indicate areas of collagen while medium gray arrows denote blood vessels. The typical distribution of muscle to collagen found in the bladder is approximately 1:1. (B) In order to demonstrate the specificity of the γ-tubulin monoclonal antibody (green) to human bladder tissue, the tissue underwent staining and all aspects of the bladder tissue including muscle and urothelium (light gray arrows) stained in a positive manner. (C) Rat bladder tissue was also stained with the γ-tubulin antibody with no apparent positive signal present (light gray arrows depict urothelium). This image is representative of eight different rat bladders stained with γ-tubulin. (D) Lastly, a human (MSCs)/rat hybrid bladder tissue was stained with the γ-tubulin antibody and clearly demonstrates the demarcation between human and rat tissue. Suture artifacts (holes, indicated by white arrows) and the POC scaffold itself were also used for orientation purposes. It has also been previously demonstrated that the γ-tubulin antibody is non-reactive with rat bladder tissue. Far left arrow indicates human tissue while the gray arrow indicates rat tissue. Figure B-D images are counterstained with DAPI in order to visualize cell nuclei. Scale bars-200 μm.

MSC grafts demonstrated a sparse number of blood vessels 4 weeks post-augmentation while vessels appeared at greater frequencies with homogenous distribution throughout the grafted tissue of MSC/CD34+ and CD34+ grafts. Vessel diameter in these grafts was also greater compared to MSC grafts (FIG. 3A, rows 1-3; red arrows indicate blood vessels). Vessel identity was confirmed by antibody staining with vascular endothelial cell markers vWF and CD31. MSC/CD34+ groups demonstrated robust vWF+ and CD31+ blood vessels in areas of regeneration (FIG. 3A, columns I, II). Co-staining with γ-tubulin [a human-reactive antibody found to be non-reactive with rat bladder tissue (ref. 13; herein incorporated by reference in its entirety); FIG. 7B-D] demonstrated γ-tubulin+/vWF+ and γ-tubulin+/CD31+ cells within the vessel perimeter (red arrows) indicating the presence of human cells within vessels. Quantification of γ-tubulin+/CD31+ vessels in regenerated tissue were similar across cell types and donor groups (Table 3). The identification of putative angiogenic vessels by subsequent co-staining with αvβ3/CD31 and FGF9/CD31 (FIG. 3A, columns III and IV) revealed new vessels (red and white arrows, respectively). Prominent FGF9 staining in PSB MSC/CD34+ grafts surrounds a newly formed MSC-derived muscle bundle (column IV, row 3) (MSC and CD34+ grafted groups shown in FIG. 8).

TABLE 3

Quantification of blood vessels in regenerated tissue containing cells of human origin at 4 wk

| | γ-tubulin$^+$/CD31$^+$ vessels (%) | | |
|---|---|---|---|
| Group | MSC | CD34$^+$ | MSC/CD34$^+$ |
| A | 56.8 ± 2.3 | 54.1 ± 3.6 | 62.3 ± 3.8 |
| PC | 52.3 ± 4.4 | 51.4 ± 4.3 | 61.5 ± 4.0 |
| PSB | 58.5 ± 6.8 | 52.3 ± 4.3 | 64.7 ± 4.3 |

To determine the cellular makeup of new blood vessels in areas of bladder tissue regeneration, tissue samples from all donor samples containing either MSCs, CD34$^+$ HSPCs, or MSC/CD34$^+$ HSPCs were quantified for γ-tubulin$^+$/CD31$^+$ blood vessels 4 wk postaugmentation. Data revealed overlapping levels of γ-tubulin$^+$/CD31$^+$ blood vessels in each cell type used with a slight increase in the levels found within MSC/CD34$^+$ groups. Data suggest varying degrees of involvement of MSCs and CD34$^+$ HSPCs in new vessel formation. Data are represented as the number of total γ-tubulin$^+$/CD31$^+$ vessels/total number of CD31$^+$ vessels. Data were obtained by manual counting of positively stained vessels.

Figure 3B:
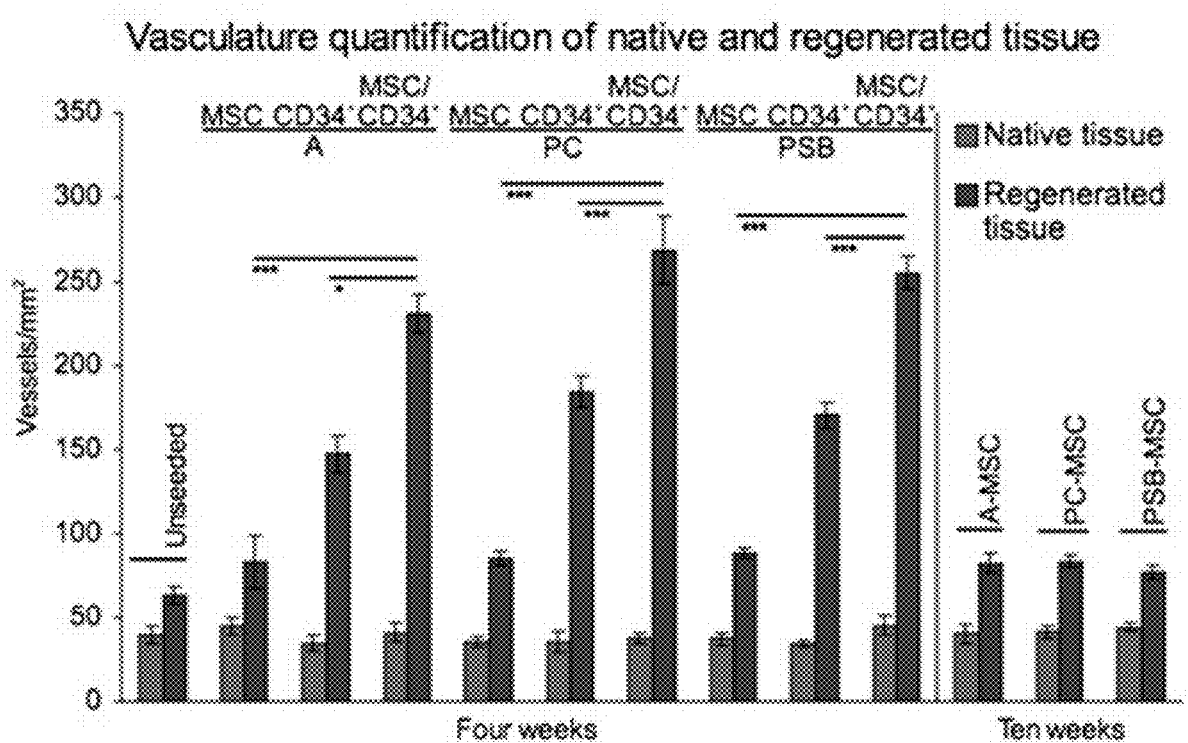

Analysis of native tissue adjacent to grafts showed a similar number of vessels and total vasculature across all 4 and 10 week groups (Table 4). No significant differences in vascularization of native tissue with respect to time (4 vs. 10 weeks), donor (A vs. PC vs. PSB) or cell type (MSC vs. CD34+vs. MSC/CD34+) (native vessel number and percent vasculature comparisons, all ns at p>0.05) were observed (FIG. 3B). Vascularization of regenerated tissue in MSC group grafts showed no indication of time or donor effects. Groups showed similar numbers of vessels, a similar level of total vasculature in areas of regenerated tissue, and a similar relationship between native and regenerated tissue. Mean vessel numbers for regenerated tissue were ~1.7-2.4× greater than mean vessel numbers for native tissue, with increases of 1.9-2.4× at 4 weeks and 1.7-2.1× at 10 weeks. In comparison, CD34+ group grafts showed enhanced vascularization in regenerated tissue, with mean vessel numbers ~4.2-5.2× greater than mean vessel numbers for native tissue. Mean percent vasculature levels were also greater than seen with MSC grafts, showing a slight increase over native tissue (FIG. 3B, C). MSC/CD34+ populations resulted in graft vascularization markedly different from all MSC groups, and with a significant increase above CD34+ group levels. Regenerated tissue in grafts from MSC/CD34+ groups exhibited significantly higher numbers of vessels/mm2 and higher percent vasculature. The relationship between native and regenerated tissue was also altered. A higher degree of increase was seen for vessel number, with mean vessel numbers for regenerated tissue ~5.6-7.2× the mean number of vessels in native tissue. Additionally, the regenerated areas of MSC/CD34+ grafts demonstrated levels of percent vasculature significantly higher than the levels in native tissue. This native/regenerated percent vasculature relationship is the converse of that seen in the MSC groups, each of which showed mean percent vasculature levels to be lower in regenerated tissue than in native tissue. No significant differences were detected between the adult and pediatric MSC/CD34+ groups in any aspect of the vascular quantification (FIG. 3B, C).

Figures 4A, 4B:
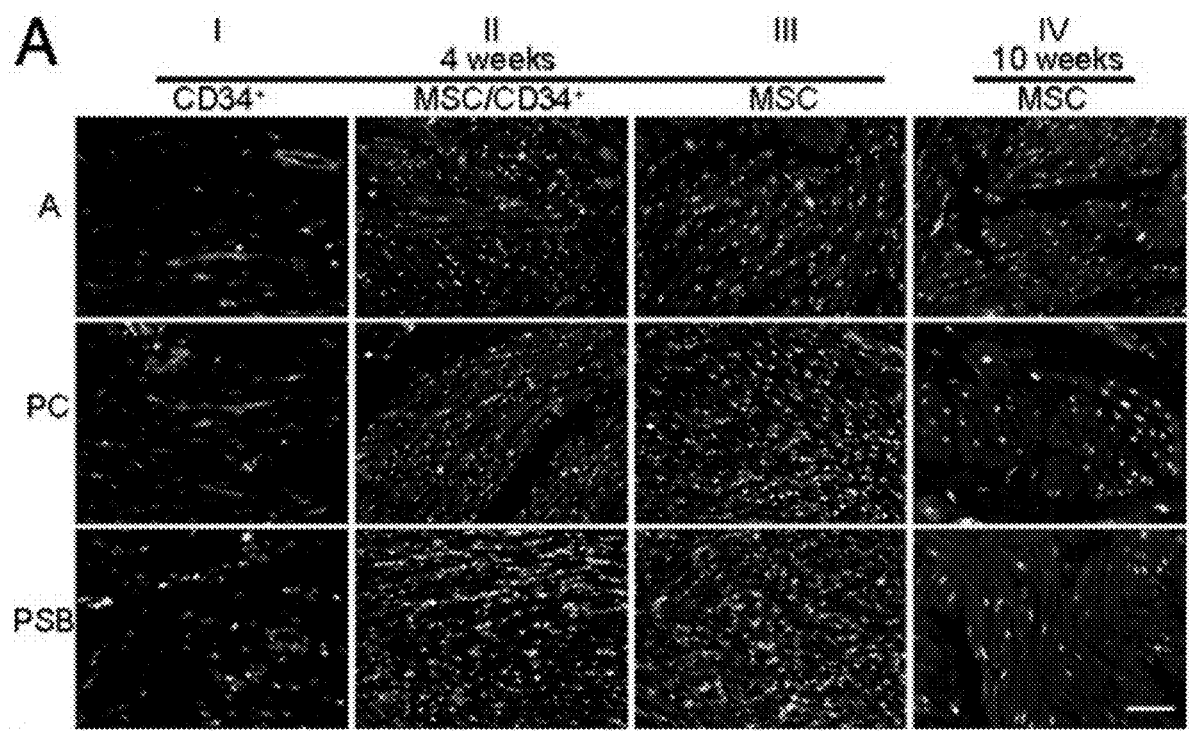
FIG. 4A-B shows proliferation index of grafted cells in regenerating tissue. (A) Ki-67 expression and γ-tubulin expression was examined in regenerating tissue amongst all groups. Fewer grafted cells were detected in CD34+ groups (column I), and fewer of the identified grafted cells expressed Ki-67. MSC/CD34+ and MSC groups (columns II, III) retained a substantive population of grafted cells, with similar Ki-67 expression. MSC groups at 10 weeks showed unchanged retention of grafted cells, but with decreased levels of proliferation. Images are representative of multiple samples/animals within a group. 400× magnification; scale bar-50 μm. (B) Ki-67+ cells shown as percentage of total grafted cells (mean±SE). Proliferation levels showed cell type and time point effects, with lower levels in CD34+ groups at 4 weeks and a decrease in levels from 4 to 10 weeks for the MSC groups (*p<0.01**p<0.0001 for MSC groups 4 vs. 10 weeks).

II, III) retained a substantive population of grafted cells, with similar levels of Ki-67 expression for both cell types. MSC groups at 10 weeks (column IV) showed unchanged retention of grafted cells, but with decreased levels of proliferation. Grafted cells from all CD34+ groups subjectively demonstrated lower levels of Ki-67 expression compared to MSC and MSC/CD34+ groups which was corroborated by quantitative analysis (FIG. 4B). Proliferation levels showed cell type and timepoint effects, with lower levels in CD34+ groups at 4 weeks (A-CD34+7.7±3.9%, PC-CD34+ 11.1±1.2%, PSB-CD34+9.2±1.7%) and increased levels in MSC containing groups (A-MSC/CD34+60.4±1.0%, PC-MSC/CD34+62.6±1.3%, PSB-MSC/CD34+64.4±0.9%, A-MSC 65.5±0.8%, PC-MSC 64.8±1.0%, PSB-MSC 66.4±0.8%). MSC groups examined at 4 and 10 weeks further demonstrated a 2.7-2.8× decrease in mean Ki-67 expression with A-MSC 24.0±1.5%, PC-MSC 23.3±0.9%, PSB-MSC 24.6±1.1%. In contrast to graft muscle content, grafted cell proliferation levels for the combination MSC/CD34+ groups at 4 weeks were consistent with MSC group levels at the earlier rather than the later timepoint (FIG. 4B).

TABLE 4

Vessel quantification for native and regenerated bladder tissue

| Bladder tissue | Unseeded | Group, 4 wk A | | | Group, 10 wk A |
| --- | --- | --- | --- | --- | --- |
| | | MSC | CD34+ | MSC/CD34+ | MSC |
| Native tissue (vessels/mm²) | 39.7 ± 5.5 | 44.8 ± 5.0 | 34.8 ± 5.1 | 41.1 ± 5.5 | 40.3 ± 5.6 |
| Regenerated tissue (vessels/mm²) | 63.8 ± 5.4 | 83.4 ± 15.8*** | 147.8 ± 11.0* | 230.9 ± 11.4 | 82.7 ± 5.5 |

| Bladder tissue | PC | | | PC |
| --- | --- | --- | --- | --- |
| | MSC | CD34+ | MSC/CD34+ | MSC |
| Native tissue (vessels/mm²) | 35.5 ± 2.8 | 35.3 ± 6.0 | 37.5 ± 3.0 | 41.5 ± 3.5 |
| Regenerated tissue (vessels/mm²) | 85.4 ± 4.4*** | 184.4 ± 9.3*** | 269.2 ± 19.8 | 83.4 ± 3.6 |

| Bladder tissue | PSB | | | PSB |
| --- | --- | --- | --- | --- |
| | MSC | CD34+ | MSC/CD34+ | MSC |
| Native tissue (vessels/mm²) | 37.2 ± 3.8 | 34.4 ± 1.8 | 45.3 ± 5.4 | 44.2 ± 2.5 |
| Regenerated tissue (vessels/mm²) | 88.7 ± 3.4*** | 170.4 ± 7.8*** | 255.7 ± 10.2 | 77.1 ± 3.9 |

In Vivo Graft Evaluation

Figure 9:
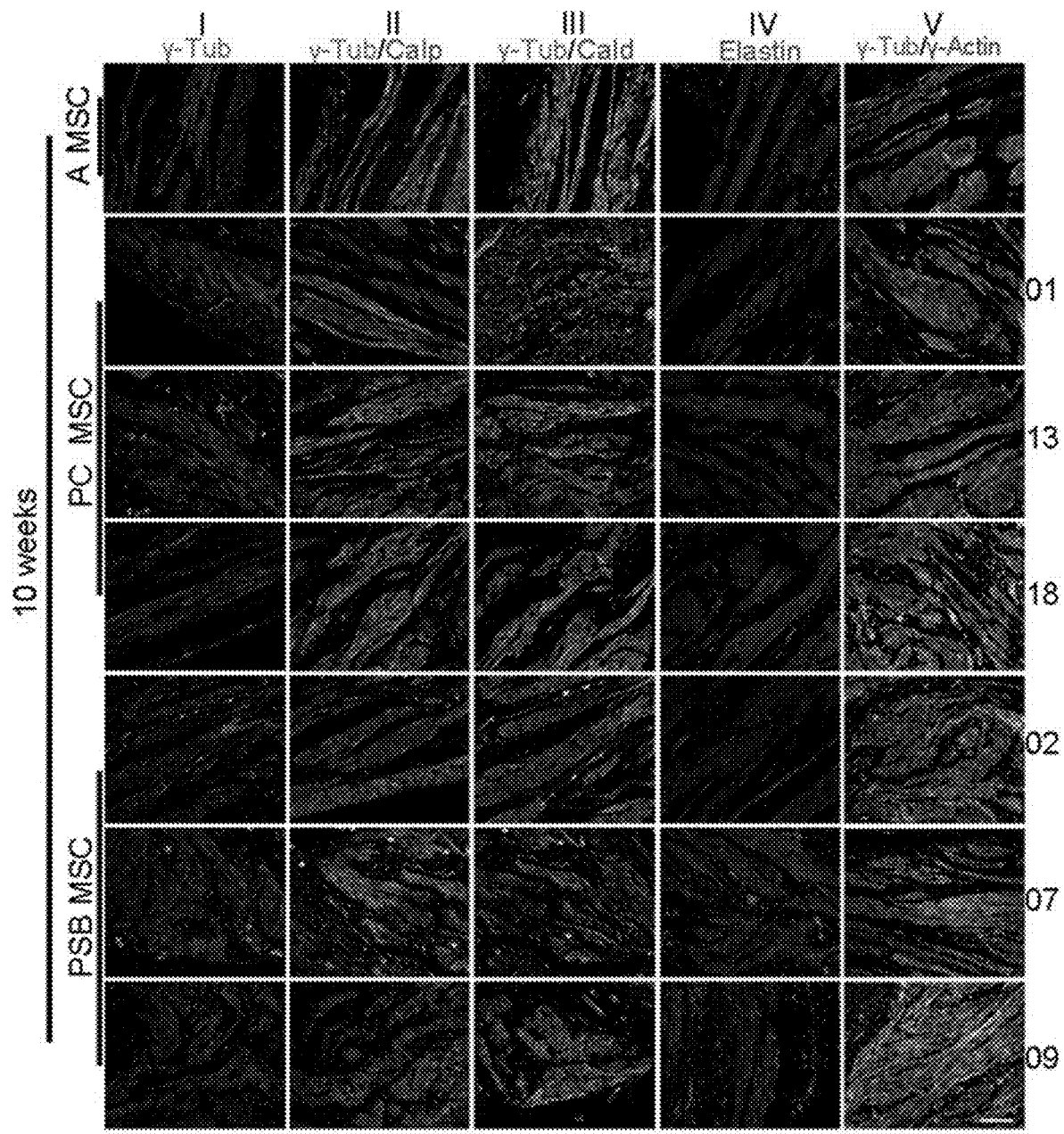
FIG. 9 shows regenerated tissue in MSC grafts. The structural protein γ-tubulin organizes microtubules within the nucleus and cytoplasm and is essential during cell division. Column I represents images of A, PC, and PSB samples expressing γ-tubulin within the regenerated area of POC/MSC seeded samples. The homogenous distribution of human-reactive γ-tubulin indicates that implanted human MSCs were retained within the graft 10 weeks post-augmentation with similar expression levels across groups based upon subjective evaluation. Hence, the expression of γ-tubulin was not altered by the SB disease process. Similarly, calponin (a marker of smooth muscle cell differentiation and regulator of smooth muscle contraction) and caldesmon (expressed on thin filaments of smooth muscle cells) when utilized in conjunction with γ-tubulin (columns II and III, respectively) again stain in a manner appearing consistent within the tissue demonstrating co-localized expression of both markers. This distribution and co-localization is also evident utilizing the human specific elastin (a key protein in bladder contraction) antibody and smooth muscle I-actin antibody paired with γ-tubulin. All samples demonstrated the morphological appearance of smooth muscle fascicles at 10 weeks post-augmentation. Scale bars=100 µm.
Figure 10A:
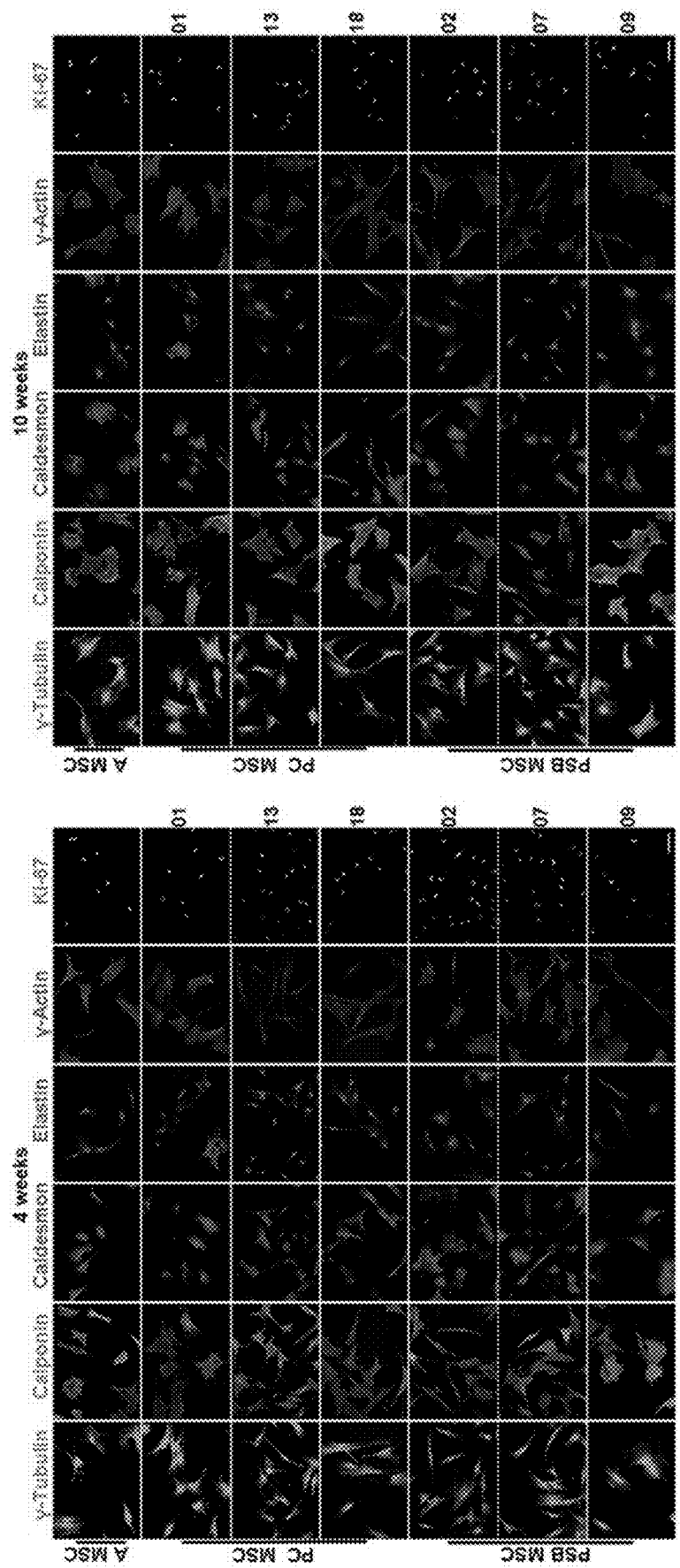
FIG. 10A shows in vitro MSC culturing. As several contractile proteins found in bladder smooth muscle cells are pivotal for overall, coordinated bladder contraction, the expression of these contractile proteins was also apparent in MSCs in vitro. Immunostaining with a battery of antibodies against these proteins demonstrated strong expression at 4 and 10 weeks of culture amongst A, PC (donors 01, 13, 18), and PSB (donors 02, 07, 09) groups. Cell proliferation as subjectively measured by Ki-67 expression also demonstrated high proliferative capacity of these cells even after 10 weeks in culture. Ki-67 images are counterstained with DAPI in order to visualize cell nuclei. Scale bar-50 µm.
Figure 10B:
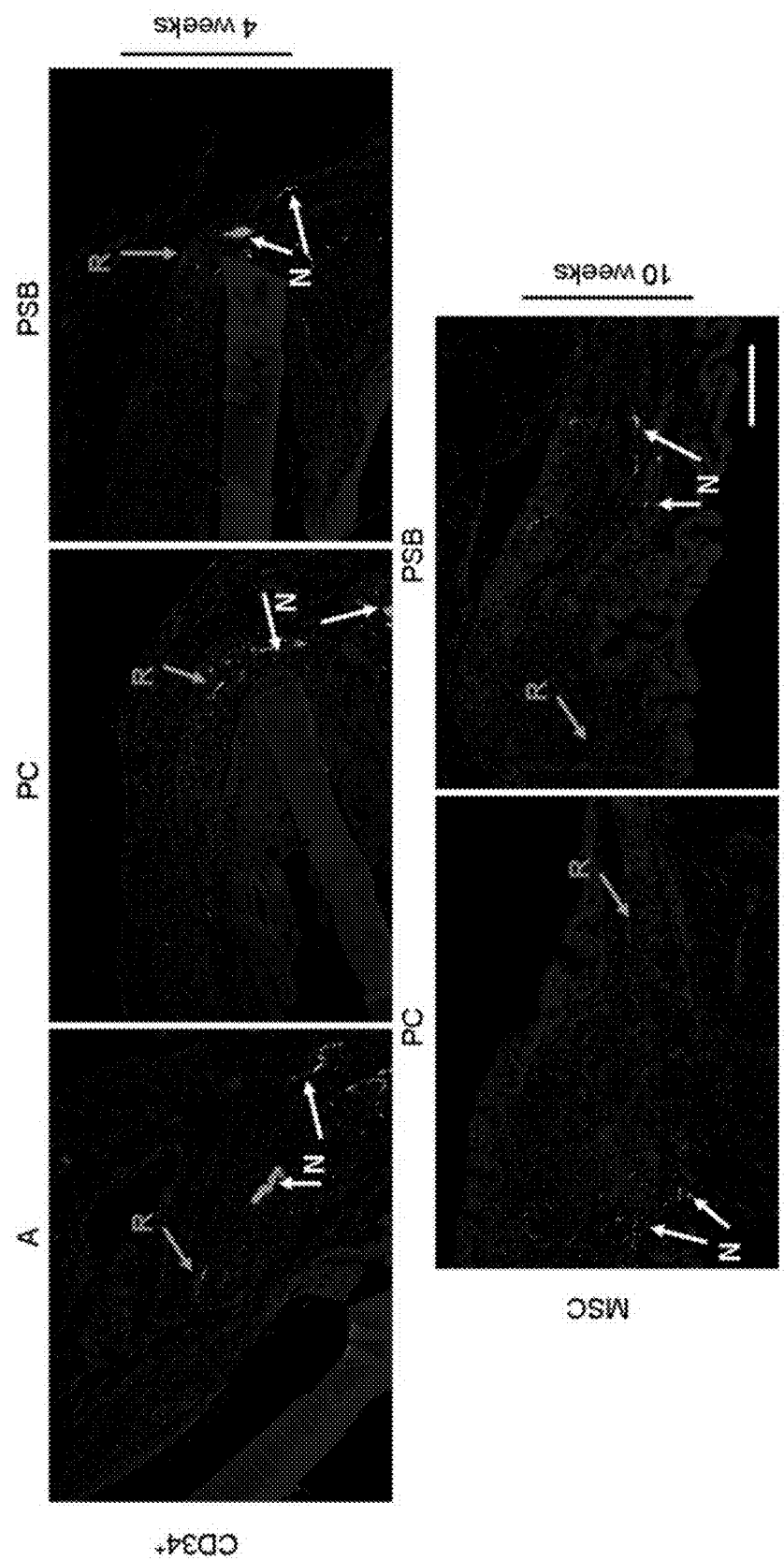
FIG. 10 B shows MSC/CD34$^+$ HSPC effect on bladder peripheral nerve growth. Micturition cycles of the bladder are in part governed by action potentials conducted through peripheral nerves encompassing the entirety of the bladder. The process of bladder cystectomy destroys these conduits thus severely hampering the degree of bladder contractility. Currently, bladder peripheral nerve regeneration has not been conclusively demonstrated. The augmentation of CD34$^+$ HSPC seeded POC scaffolds provide minor peripheral nerve regeneration in A, PC, and PSB donor samples at 4 weeks post-augmentation. Neuronal specific βIII tubulin staining (green) demonstrates minimal peripheral nerve staining at the border of areas of regenerated tissue (denoted as a green "R") and areas of native tissue (denoted by a white "N") (row 1). MSC seeded POC scaffolds at 10 weeks post-augmentation demonstrated the lack of peripheral nerves in the regenerated area as demonstrated by βIII tubulin staining for PC and PSB samples (row 2). Areas of regeneration were determined by POC scaffold boundaries and locations of suture markings. Images are representative of multiple donor groups (in the case of PC and PSB) along with multiple animals. Images are counterstained with DAPI (blue) in order to visualize cell nuclei. Scale bar-500 µm

Bladder muscle is composed of specialized smooth muscle cells (SMCs) expressing several key proteins for repetitive contraction/expansion cycles. MSC seeded grafts demonstrated the morphological appearance of smooth muscle fascicles and grafted MSCs exhibited expression of these smooth muscle proteins 10 weeks post-augmentation (FIG. 9) as well as 4 and 10 weeks in vitro (FIG. 10A). In vivo cell proliferation was assessed by Ki-67 expression (green) in grafted cell populations along with γ-tubulin expression (red) in regenerating tissue amongst all donor groups (FIG. 4A). At 4 weeks post-augmentation, comparably fewer grafted cells were detected in CD34+ groups (column I), and fewer of the identified grafted cells expressed Ki-67. MSC/CD34+ and MSC groups (columns Peripheral Nerve Regeneration with MSC/CD34+Grafts To determine the effect of MSC/CD34+ seeded POC grafts on bladder peripheral nerve regeneration, explanted bladder tissue consisting of adjoining native and regenerated tissue areas was stained with neuronal-specific antibodies βIII tubulin and synaptophysin. Adult MSC seeded scaffolds revealed expression of βIII tubulin (green) in native tissue at all timepoints, although its expression was absent in regenerated tissue at 4 and 10 weeks (FIG. 5A, B) with nominal expression at 20 weeks post-augmentation (FIG. 5C: white and green arrows depict native and regenerated areas, respectively). However, 4 week MSC/CD34+ grafts exhibited an abundance of peripheral nerve growth emanating from native tissue and traversing regenerated tissue as confirmed independently by βIII tubulin (green; FIG. 5D-F)

and synaptophysin staining (red; FIG. 5G-I). Co-staining with γ-tubulin revealed that putative nerve bundles (NB) were of rodent origin. γ-tubulin+ tissue adjacent to NB consisted of muscle fascicles comprised of grafted human cells (red, FIG. 5D-F; green, FIG. 5G-I, respectively). NB in regenerating tissue populated by grafted cells were detected in all MSC/CD34+ samples (FIG. 5: A-D, G; PC-E, H; PSB-F, I). In the absence of MSCs, CD34+ grafts at 4 weeks showed minimal neuronal marker expression in regenerated areas at 4 weeks (FIG. 10B). The MSC/CD34+>CD34+>MSC trend observed with peripheral nerve regeneration is analogous to that of vasculature in regenerating tissue.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the present invention.

REFERENCES

The publications listed below, referenced by number, are herein incorporated by reference in their entireties.

1. Greene N D, Stanier P, Copp A J. (2009) Genetics of human neural tube defects. Hum Mol Genet 8:R113-R129.
2. Bebbington M W, Danzer E, Johnson M P, Adzick, N S. (2011) Open fetal surgery for myelomeningocele. Prenat Diagn. 31:689-694.
3. Clayton D B, Brock J W 3rd, Joseph D B. (2010) Urologic management of spina bifida. Dev Disabil Res Rev 16:88-95.
4. Atala A, Bauer S B, Soker S, Yoo J J, Retik A B. (2006) Tissue-engineered autologous bladders for patients needing cystoplasty. Lancet 367:1241-1246.
5. Guven A, Onal B, Kogan B A. (2006) Spontaneous bladder perforations following augmentation cystoplasty in children. Nat Clin Pract Urol 3:584-585.
6. Flood H D, et al. (1995) Long-term results and complications using augmentation cystoplasty in reconstructive urology. Neurourol Urodyn 14:297-309.
7. Austin J C. (2008) Long-term risks of bladder augmentation in pediatric patients. Curr Opin Urol. 18:408-412.
8. Baum C M, Weissman I L, Tsukamoto A S, Buckle A M, Peault B. (1992) Isolation of a candidate human hematopoietic stem-cell population. Proc Natl Acad Sci USA 89:2804-2808.
9. Losordo D W, et al. (2007) Intramyocardial transplantation of autologous CD34+ stem cells for intractable angina: a phase I/IIa double-blind, randomized controlled trial. Circulation 115:3165-3172.
10. Pittenger M F, et al. (1999). Multilineage potential of adult human mesenchymal stem cells. Science 284:143-147.
11. Ishikane S, et al. (2008) Allogeneic injection of fetal membrane-derived mesenchymal stem cells induces therapeutic angiogenesis in a rat model of hind limb ischemia. Stem Cells 26:2625-2633.
12. Heinrich M, Oberbach A, Schlichting N, Stolzenburg J-U, Neuhaus J. (2011) Cytokine effects on gap junction communication and connexin expression in human bladder smooth muscle cells and suburothelial myofibroblasts. PLoS ONE 6:e20792.
13. Sharma A K, et al. (2010) Urinary bladder smooth muscle regeneration utilizing bone marrow derived mesenchymal stem cell seeded elastomeric poly(1,8-octanediol-co-citrate) based thin films. Biomaterials 31:6207-6217.
14. Hoogduijn M J, Cheng A, Genever P G. (2009) Functional nicotinic and muscarinic receptors on mesenchymal stem cells. Stem Cells Dev 18:103-112.
15. Sharma A K, et al. (2009) Defined populations of bone marrow derived mesenchymal stem and endothelial progenitor cells for urinary bladder regeneration. J Urol 182:1898-1905.
16. Nagatomi J, Toosi K K, Grashow J S, Chancellor M B, Sacks M S. (2005) Quantification of bladder smooth muscle orientation in normal and spinal cord injured rats Ann Biomed Eng. 33:1078-1089.
17. Takeda K, et al. (1998) Normal bladder wall morphology in Gd-DTPA-enhanced clinical MR imaging using an endorectal surface coil and histological assessment of submucosal linear enhancement using [14C] Gd-DOTA autoradiography in an animal model. Eur J Radiol 26:290-296.
18. Shin K, et al. (2011) Hedgehog/Wnt feedback supports regenerative proliferation of epithelial stem cells in bladder. Nature 472:110-114.
19. Van Den Berg D J, Sharma A K, Bruno E, Hoffman R. (1998) Role of members of the Wnt gene family in human hematopoiesis. Blood 92:3189-3202.
20. Cathey L, Lee K Y, Holder W. D, Mooney D J, Halberstadt C R. (2007) in Principles of Tissue Engineering (Third Edition), eds Lanza R, Langer R, Vacanti J. (Elsevier, USA), pp 528-530.
21. Stegemann J P, Kaszuba S N, Rowe S L. (2007) Review: advances in vascular tissue engineering using protein-based biomaterials. Tissue Eng 13:2601-2613.
22. Sahoo S, et al. (2011) Exosomes from human CD34(+) stem cells mediate their proangiogenic paracrine activity. Circ Res. 109:724-728.
23. Losordo D W, et al. (2011) Intramyocardial, autologous CD34+ cell therapy for refractory angina. Circ Res 109:428-436.
24. Bexell D, et al. (2009) Bone marrow multipotent mesenchymal stroma cells act as pericyte-like migratory vehicles in experimental gliomas. Mol Ther 17:183-190.
25. Scheubel R J, et al. (2010) Paracrine effects of CD34 progenitor cells on angiogenic endothelial sprouting. Int J Cardiol. 139:134-141.
26. Tei K, et al. (2008) Administrations of peripheral blood CD34-positive cells contribute to medial collateral ligament healing via vasculogenesis. Stem Cells 26:819-830.
27. Murphy E A, et al. (2008) Nanoparticle-mediated drug delivery to tumor vasculature suppresses metastasis. Proc Natl Acad Sci USA 105:9343-9348.
28. Frontini M J, et al. (2011) Fibroblast growth factor 9 delivery during angiogenesis produces durable, vasoresponsive microvessels wrapped by smooth muscle cells. Nat Biotechnol 29:421-427.
29. Xiao C G, et al. (2003) An artificial somatic-central nervous system-autonomic reflex pathway for controllable micturition after spinal cord injury: preliminary results in 15 patients. J Urol 2003 170:1237-1241.
30. Steidl U, et al. (2004) Primary human CD34+ hematopoietic stem and progenitor cells express functionally active receptors of neuromediators. Blood 104:81-88.

31. Bracci-Laudiero L, et al. (2003) CD34-positive cells in human umbilical cord blood express nerve growth factor and its specific receptor TrkA. J Neuroimmunol 136:130-139.
32. Mezey E, et al. (2000) Turning blood into brain: cells bearing neuronal antigens generated in vivo from bone marrow. Science 290:1779-1782.
33. Spiegel A, et al. (2007) Catecholaminergic neurotransmitters regulate migration and repopulation of immature human CD34+ cells through Wnt signaling. Nat Immunol 8:1123-1131.
34. Gao J, et al. (2006) A neuroinductive biomaterial based on dopamine. Proc Natl Acad Sci USA. 103:16681-16686.
35. Guys J, et al. (2004) Sacral neuromodulation for neurogenic bladder dysfunction in children. J Urol. 172:1673-1676.
36. Choi E, et al. (2012) Effects of intravesical electrical stimulation therapy on urodynamic patterns for children with spina bifida: A 10-year experience. J Pediatr Urol. S1477-5131(12)00257-4.

The invention claimed is:

1. A system comprising:
   (a) a synthetic elastomeric scaffold for supporting and transplantation of cells,
   (b) a cell population of isolated mesenchymal stem cells (MSCs), wherein greater than 90% of the MSCs are $CD29^+$, $CD44^+$, $CD73^+$, $CD90^+$, $CD105^+$, $CD166^+$, $CD14^-$, $CD34^-$, $CD45^-$, $CD117^-$, and $CD133^-$; and
   (c) a cell population of hematopoietic stem/progenitor cells (HSPCs), wherein greater than 90% of the HSPCs are $CD34^+$.

2. The system of claim 1, wherein said scaffold comprises a poly(citrate diol).

3. The system of claim 1, wherein said isolated MSCs are bone marrow mesenchymal cells.

4. The system of claim 1, wherein said scaffold is impregnated with said cell population of isolated MSCs and said cell population of HSPCs.

5. A method of tissue regeneration comprising administering to a subject in need of tissue repair the system of claim 1.

6. The method of claim 5, wherein said scaffold comprises a poly(diol citrate).

7. The method of claim 6, wherein the scaffold comprises poly(octandediol citrate).

8. The method of claim 5, wherein said tissue is bladder tissue.

9. An article of manufacture comprising: a cell scaffold configured to be inserted into a subject, wherein said cell scaffold is impregnated with:
   (a) a cell population of isolated mesenchymal stem cells (MSCs), wherein greater than 90% of the MSCs are $CD29^+$, $CD44^+$, $CD73^+$, $CD90^+$, $CD105^+$, $CD166^+$, $CD14^-$, $CD34^-$, $CD45^-$, $CD117^-$, and $CD133^-$; and
   (b) a cell population of hematopoietic stem/progenitor cells (HSPCs), wherein greater than 90% of the HSPCs are $CD34^+$.

10. The article of manufacture of claim 9, wherein said cell scaffold is configured to be inserted into a mammalian bladder.

* * * * *